(12) United States Patent
Yu et al.

(10) Patent No.: US 10,335,113 B2
(45) Date of Patent: Jul. 2, 2019

(54) APPARATUS FOR ULTRASOUND FLOW VECTOR IMAGING AND METHODS THEREOF

(71) Applicant: VERSITECH LIMITED, Hong Kong (CN)

(72) Inventors: Alfred Cheuk Hang Yu, Hong Kong (CN); Yat Shun Yiu, Hong Kong (CN)

(73) Assignee: VERSITECH LIMITED, Hong Kong (HK)

( * ) Notice: Subject to any disclaimer, the term of this patent is extended or adjusted under 35 U.S.C. 154(b) by 0 days.

(21) Appl. No.: 15/445,582

(22) Filed: Feb. 28, 2017

(65) Prior Publication Data

US 2017/0215836 A1    Aug. 3, 2017

Related U.S. Application Data

(63) Continuation of application No. 14/544,048, filed on Nov. 19, 2014, now Pat. No. 10,231,695.
(Continued)

(51) Int. Cl.
*A61B 8/00* (2006.01)
*A61B 8/06* (2006.01)
(Continued)

(52) U.S. Cl.
CPC ............... *A61B 8/06* (2013.01); *A61B 8/02* (2013.01); *A61B 8/4494* (2013.01); *A61B 8/461* (2013.01);
(Continued)

(58) Field of Classification Search
CPC ............. A61B 8/06; A61B 8/02; A61B 8/488; A61B 8/461; A61B 8/4404; A61B 8/5207; A61B 8/5223; A61B 600/437–472
See application file for complete search history.

(56) References Cited

U.S. PATENT DOCUMENTS 5,010,528 A * 4/1991 Ohtsuki ............... A61B 8/06
                                                     367/90
5,622,174 A    4/1997 Yamazaki
(Continued)

FOREIGN PATENT DOCUMENTS

CN          102123668 A       7/2011
WO    WO 2013059659 A1 *   4/2013   ......... G01S 15/8984

OTHER PUBLICATIONS

Billy Y.S. Yiu, et al., Vector Projectile Imaging: Time-Resolved Dynamic Visualization of Complex Flow Patterns, Elsevier, World Federation for Ultrasound in Medicine & Biology, Mar. 10, 2015, pp. 2295-2309.

(Continued)

*Primary Examiner* — Joseph M Santos Rodriguez
(74) *Attorney, Agent, or Firm* — Kory D. Christensen

(57) ABSTRACT

Apparatus and methods of use are provided for complex flow imaging and analysis that is non-invasive, accurate, and time-resolved. It is particularly useful in imaging of vascular flow with spatiotemporal fluctuations. This apparatus is an ultrasound-based framework called vector projectile imaging (VPI) that can dynamically render complex flow patterns over an imaging view at millisecond time resolution. The VPI apparatus and methods comprise: (i) high-frame-rate broad-view data acquisition (based on steered plane wave firings); (ii) flow vector estimation derived from multi-angle Doppler analysis (coupled with data regularization and least-squares fitting); and (iii) dynamic visualization of color-encoded vector projectiles (with flow speckles displayed as adjunct).

14 Claims, 13 Drawing Sheets
(8 of 13 Drawing Sheet(s) Filed in Color)

Related U.S. Application Data

(60) Provisional application No. 61/905,974, filed on Nov. 19, 2013.

(51) Int. Cl.
*A61B 8/08* (2006.01)
*A61B 8/02* (2006.01)
*G01S 15/89* (2006.01)
*G01S 7/52* (2006.01)
*G01S 15/58* (2006.01)
*G06T 7/20* (2017.01)
*A61B 8/12* (2006.01)

(52) U.S. Cl.
CPC .............. *A61B 8/469* (2013.01); *A61B 8/488* (2013.01); *A61B 8/5207* (2013.01); *A61B 8/5215* (2013.01); *A61B 8/5223* (2013.01); *G01S 7/52073* (2013.01); *G01S 7/52085* (2013.01); *G01S 15/58* (2013.01); *G01S 15/8984* (2013.01); *G06T 7/20* (2013.01); *A61B 8/0891* (2013.01); *A61B 8/12* (2013.01); *G01S 15/8915* (2013.01)

(56) References Cited

U.S. PATENT DOCUMENTS

| | | | |
|---|---|---|---|
| 6,148,224 A | 11/2000 | Jensen | |
| 6,210,168 B1* | 4/2001 | Aiger | G09B 23/286 434/262 |
| 6,277,075 B1* | 8/2001 | Torp | G01S 7/52039 600/443 |
| 2007/0016050 A1* | 1/2007 | Moehring | A61B 8/06 600/454 |
| 2008/0269611 A1 | 10/2008 | Pedrizzetti et al. | |
| 2009/0326379 A1 | 12/2009 | Daigle et al. | |
| 2011/0196237 A1 | 8/2011 | Pelissier et al. | |
| 2011/0245673 A1* | 10/2011 | Kamiyama | A61B 8/08 600/443 |
| 2013/0046175 A1 | 2/2013 | Sumi | |
| 2013/0144166 A1 | 6/2013 | Specht et al. | |

OTHER PUBLICATIONS

Evans et al., "Ultrasonic Colour Doppler Imaging," Interface Focus 2011, vol. 1, pp. 490-502.

* cited by examiner

FIG. 9A
FIG. 9D
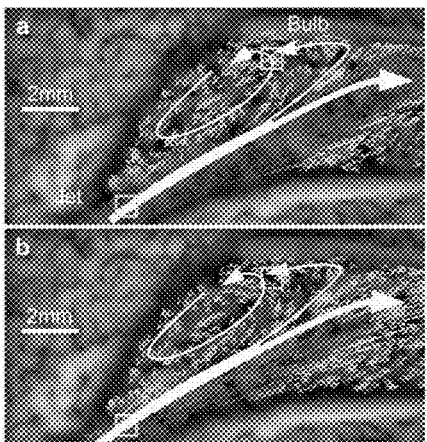
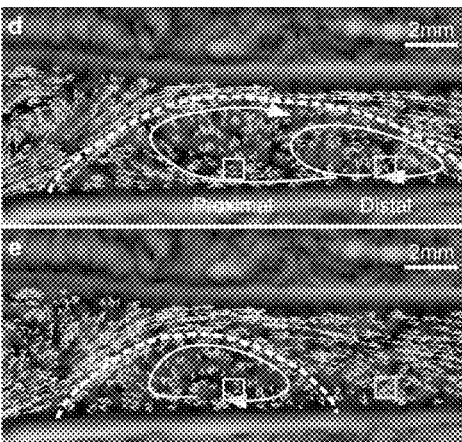
FIG. 9B
FIG. 9E
FIG. 9C
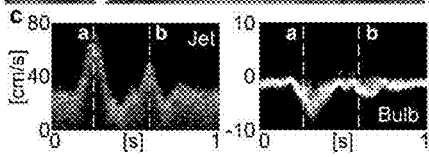
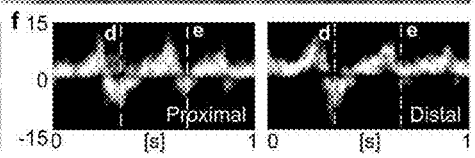
FIG. 9F

APPARATUS FOR ULTRASOUND FLOW VECTOR IMAGING AND METHODS THEREOF

The present application claims priority to U.S. Provisional Application No. 61/905,974 filed on Nov. 19, 2013, which is incorporated herein in its entirety.

TECHNICAL FIELD

The present invention is generally directed to an ultrasonic imaging system, and more particularly to an ultrasonic system for imaging vascular flow. This imaging system can be used for non-invasively visualizing the flow of blood in a human blood vessel.

BACKGROUND OF THE INVENTION

Non-invasive visualization of flow dynamics in human arteries is widely considered to be of high diagnostic importance as it may foster clinical detection of abnormal vascular conditions (Steinman D A, Taylor C A. Flow imaging and computing: large artery hemodynamics. Ann. Biomed. Eng., 2005; 33: 1704-1709). For instance, monitoring flow patterns in the carotid arteries has long been implicated in useful in stroke prognosis (Donnan G A, Fisher M, Macleod M, Davis S M. Stroke. Lancet, 2008; 371: 1612-1623; Shields R C. Medical management of carotid stenosis. Perspect. Vasc. Surg. Endovasc. Ther., 2010; 22: 18-27). Over the years, a few non-invasive flow imaging modalities have been developed (Owen A R, Roditi G H. Peripheral arterial disease: the evolving role of non-invasive imaging. Postgrad. Med. J., 2011; 87: 189-198; Wolbarst A B, Hendee W R. Evolving and experimental technologies in medical imaging. Radiology, 2006; 238: 16-39), and among them, ultrasound has perhaps established itself as a unique bedside modality that can be readily applied to point-of-care diagnoses (Bierig S M, Jones A. Accuracy and cost comparison of ultrasound versus alternative imaging modalities, including CT, MR, PET, and angiography. J. Diagnost. Med. Sonography, 2009; 25: 138-144; Moore C L, Copel J A. Point-of-care ultrasonography. New Eng. J. Med., 2011; 364: 749-757). In most existing ultrasound scanners, flow information can be rendered in real-time in the form of color flow images, which provide 2-D maps of axial flow velocity (or flow power) over an imaging view (Evans D H. Color flow and motion imaging. Proc. Inst. Mech. Eng. H, 2010; 224: 241-253; Hoskins P R, McDicken W N. Colour ultrasound imaging of blood flow and tissue motion. Br. J. Radiol., 1997; 70: 878-890). This flow imaging mode, when used together with the Doppler spectrogram mode that plots the temporal flow profile at a single range gate, can offer vast information about flow behavior in both spatial and temporal dimensions (Gaitini D, Soudack M. Diagnosing carotid stenosis by Doppler sonography: state of the art. J. Ultrasound Med., 2005; 24: 1127-1136; Hoskins P R. Haemodynamics and blood flow measured using ultrasound imaging. Proc. Inst. Mech. Eng. H, 2010; 224: 255-271).

Despite its popular role in clinical screening, ultrasound color flow imaging is known to possess method flaws (Evans 2010). In particular, as its operating principle is typically based on axial Doppler estimation, it is prone to error if the beam-flow angle (i.e. angle between the ultrasound propagation axis and the flow trajectory) varies over the vasculature (Evans D H, Jensen J A, Nielsen M B. Ultrasound color Doppler imaging. Interface Focus, 2011; 1: 490-502). This issue represents a significant pitfall in diagnostic scenarios where the vasculature is not in straight-tube form, such as the bifurcation geometry found in the carotid arteries (Ku D N. Blood flow in arteries. Annu. Rev. Fluid Mech., 1997; 29: 399-434). In these cases, it can be challenging for sonographers to properly interpret color flow images (Arning C, Eckert B. The diagnostic relevance of colour Doppler artefacts in carotid artery examinations. Eur. J. Radiol., 2004; 51: 246-251; Rubens D J, Bhatt S, Nedelka S, Cullinan J. Doppler artifacts and pitfalls. Radiol. Clin. N. Am., 2006; 44: 805-835), especially when exacerbated by pulsatile flow conditions with considerable temporal variations in flow velocities.

For ultrasound to succeed in providing unambiguous mapping of flow dynamics in tortuous vasculature, it is imperative to resolve the beam-flow angle dependence problem and in turn derive velocity estimates that reflect the actual flow characteristics (Dunmire B, Beach K W, Labs K H, Plett M, Strandness Jr D E. Cross-beam vector Doppler ultrasound for angle-independent velocity measurements, Ultrasound Med. Biol., 2000, 26: 1213-1235; Tortoli P, Bambi G, Ricci S. Accurate Doppler angle estimation for vector flow measurements. IEEE Trans. Ultrason. Ferroelec. Freq. Contr., 2006; 53: 1425-1431; Tortoli P, Dallai A, Boni E, Francalanci L, Ricci S., "An automatic angle tracking procedure for feasible vector Doppler blood velocity measurements," Ultrasound Med. Biol. (2010), 36: 488-496). To fulfill this task, flow estimation needs to be performed not only along the axial direction (as is the case in color flow imaging) but also the lateral direction of the imaging view, so that both the flow angle and the velocity magnitude can be determined without uncertainty (Evans et al. 2011). Motivated by such rationale, new imaging paradigms for flow vector estimation have been proposed. Often categorized as vector flow imaging methods, these paradigms are generally based on four types of estimation principles: (i) multi-angle Doppler analysis (Capineri L, Scabia M, Masotti L. A Doppler system for dynamic vector velocity maps. Ultrasound Med. Biol., 2002; 28: 237-248; Kripfgans O D, Rubin J M, Hall A L, Fowlkes J B. Vector Doppler imaging of a spinning disc ultrasound Doppler phantom. Ultrasound Med. Biol., 2006; 32: 1037-1046; Pastorelli A, Torricelli G, Scabia M, Biagi E, Masotti L. A real-time 2-D vector Doppler system for clinical experimentation. IEEE Trans. Med. Imag., 2008; 27: 1515-1524; (ii) biaxial phase shift estimation from acoustic fields with transverse oscillations (Pedersen M M, Pihl M J, Haugaard P, Hansen J M, Hansen K L, Nielsen M B, Jensen J A. Comparison of real-time in vivo spectral and vector velocity estimation. Ultrasound Med. Biol., 2012; 39: 145-151; Udesen J, Jensen J A. Investigation of transverse oscillation method. IEEE Trans. Ultrason. Ferroelec. Freq. Contr., 2006; 53: 959-971; Udesen J, Nielsen M B, Nielsen K R, Jensen J A. Examples of in vivo blood vector velocity estimation. Ultrasound Med. Biol., 2007; 33: 541-548); (iii) inter-frame blood speckle tracking (Bohs L N, Geiman B J, Anderson M E, Gebhart S C, Trahey G E. Speckle tracking for multi-dimensional flow estimation. Ultrasonics, 2000; 38: 369-375; Ebbini E S. Phase-coupled two-dimensional speckle tracking algorithm. IEEE Trans. Ultrason. Ferroelec. Freq. Contr., 2006; 53: 972-990; Xu T, Bashford G R. Two-dimensional blood flow velocity estimation using ultrasound speckle pattern dependence on scan direction and A-line acquisition velocity. IEEE Trans. Ultrason. Ferroelec. Freq. Contr., 2013; 60: 898-908); and (iv) directional cross-correlation analysis (Jensen J A. Directional velocity estimation using focusing along the flow direction I: theory and simulation. IEEE Trans. Ultrason. Ferroelec. Freq.

Contr., 2003; 50: 857-872; Jensen J A, Bjerngaard R. Directional velocity estimation using focusing along the flow direction II: experimental investigation. *IEEE Trans. Ultrason. Ferroelec. Freq. Contr.*, 2003; 50: 873-880; Kortbek J, Jensen J A. Estimation of velocity vector angles using the directional cross-correlation method. *IEEE Trans. Ultrason. Ferroelec Freq. Contr.*, 2006; 53: 2036-2049). While each of these approaches has its own merit, they are all known to yield erroneous flow vector estimates under certain scenarios. Notably, Doppler/phase-shift estimation is prone to aliasing artifacts when tracking fast flow, whereas speckle tracking and directional cross-correlation have difficulty in following out-of-plane motion (Hansen L K, Udesen J, Oddershede N, Henze L, Thomsen C, Jensen J A, Nielsen M B. In vivo comparison of three ultrasound vector velocity techniques to MR phase contrast angiography. *Ultrasonics*, 2009; 49: 659-667; Swillens A, Segers P, Torp H, Lovstakken L. Two-dimensional blood velocity estimation with ultrasound: speckle tracking versus crossed-beam vector Doppler based on flow simulations in a carotid bifurcation model. *IEEE Trans. Ultrason. Ferroelec. Freq. Contr.*, 2010a; 57: 327-339). These frailties are particularly exposed when flow velocities vary significantly over different phases of a pulsatile flow cycle and when the imaging frame rate is inadequate (Swillens A, Segers P, Lovstakken L. Two-dimensional flow imaging in the carotid bifurcation using a combined speckle tracking and phase-shift estimator: a study based on ultrasound simulations and in vivo analysis. *Ultrasound Med. Biol.*, 2010b; 36: 1722-1735).

SUMMARY OF THE INVENTION

The present invention is directed to an apparatus and methods for imaging and complex analysis of vascular flow with spatiotemporal fluctuations that is non-invasive, accurate, and time-resolved. In particular, the invention is a new ultrasound-based framework that can be called "Vector Projectile Imaging" (VPI), which dynamically renders complex flow patterns over an imaging view at millisecond time resolution. VPI is founded upon three principles: (i) high-frame-rate broad-view data acquisition (based on steered plane wave firings); (ii) flow vector estimation derived from multi-angle Doppler analysis (coupled with data regularization and least-squares fitting); and (iii) dynamic visualization of color-encoded vector projectiles (with flow speckles displayed as an adjunct).

VPI can enable quantitative and consistent tracking of spatiotemporally varying flow trajectories in curvy vascular geometries like the carotid bifurcation. The present invention is more advanced than current methods. In particular, the present invention has duplex mode flow information, including velocity-encoded flow projectiles (instead of just a particle) and flow speckles. The present invention utilizes new methods for both data processing and rendering to support consistent flow estimation. In designing VPI, consistent flow vector estimation performance is achieved through the integrative use of: (i) broad-view insonation schemes that can readily offer high data acquisition frame rates well beyond the video display range; and (ii) multi-angle Doppler analysis coupled with post-hoc regularization strategies and least-squares estimation principles. Furthermore, provided that high imaging frame rates and consistent flow vector estimates are available, it is estimated that dynamic visualization of flow vectors can be made possible through rendering them in a duplex form that depicts: (i) particle projectiles, which quantitatively highlight the local flow speed, orientation, and trajectory; and (ii) flow speckles, which serve as a qualitative adjunct to enhance visualization effect.

The present invention is readily distinguished from earlier efforts that showed the feasibility of achieving high-frame-rate vector flow imaging through spherical wave firings (Nikolov S I, Jensen J A. In-vivo synthetic aperture flow imaging in medical ultrasound. *IEEE Trans. Ultrason. Ferroelec. Freq. Contr.*, 2003; 50: 848-856; Oddershede N, Jensen J A. Effects influencing focusing in synthetic aperture vector flow imaging. *IEEE Trans. Ultrason. Ferroelec. Freq. Contr.*, 2007; 54: 1811-1825) or plane wave excitation (Ekroll I K, Swillens A, Segers P, Dahl T, Torp H, Lovstakken L. Simultaneous quantification of flow and tissue velocities based on multi-angle plane wave imaging. *IEEE Trans. Ultrason. Ferroelec. Freq. Contr.*, 2013; 60: 727-738; Flynn J, Daigle R, Pflugrath L, Linkhart K, Kaczkowski P. Estimation and display for vector Doppler imaging using plane wave transmissions. *Proc. IEEE Ultrason. Symp.*, 2011; 413-418, Flynn J, Daigle R, Pflugrath L, Kaczkowski P. High frame rate vector velocity blood flow imaging using a single plane wave transmission angle. *Proc. IEEE Ultrason. Symp.*, 2012; 323-325; Lu J Y, Wang Z, Kwon S J. Blood flow velocity vector imaging with high frame rate imaging methods. *Proc. IEEE Ultrason. Symp.*, 2006; 963-967; Udesen J, Gran F, Hensen K L, Jensen J A, Thomsen C, Nielsen M B. High frame-rate blood vector velocity imaging using plane waves: simulations and preliminary experiments. *IEEE Trans. Ultrason. Ferroelec. Freq. Contr.*, 2008; 55: 1729-1743). As will be demonstrated through an anthropomorphic flow phantom validation study, VPI represents an imaging innovation that uniquely couples high-frame-rate data acquisition, regularized flow vector estimation, and novelties in dynamic visualization.

VPI has the following key features that distinguish it from conventional color flow imaging (CFI): 1) Can readily offer imaging frame rates well beyond video display range (e.g. >1,000 fps); 2) Provides estimates of flow velocity vectors to account for multi-directional flow components; 3) Projectile-based rendering of flow vectors to highlight their spatiotemporal dynamics. These features are made possible through a unique marriage of broad-view data acquisition principles, flow vector analysis algorithms, and novelties in computer vision.

The steps of the technique of the present invention include data acquisition, regularized flow vector estimation, and dynamic visualization. Each of the steps can be briefly summarized as follows.

1. Data Acquisition:

VPI is based on the use of M steered plane waves[1] during ultrasonic transmission (Tx). For each Tx angle, parallel beam-forming for a 2-D image grid is performed over N dynamic receive (Rx) steering angles. The M-Tx pulsing scheme is looped repeatedly as analogous to slow-time sampling in Doppler. The effective frame rate for VPI is then simply equal to $FR=f_{PW}/M$, where $f_{PW}$ is the rate of each plane wave firing event (i.e. equal to the pulse repetition frequency, or PRF). By simply adjusting PRF, the FR can be boosted to >1,000 fps as needed to track fast-changing flow. Note that, for each pixel $P_o$ within the 2-D image grid, there are MN beam-formed ensembles along slow-time (i.e. MN number of 1-D slow-time signal arrays; each corresponding to one combination of Tx-Rx angle).

2. Regularized Flow Vector Estimation:

This process is performed independently for individual pixels. In every realization, the process can be divided into two stages: (i) velocity estimation for each of the MN slow-time ensembles for that pixel; (ii) vector computation via least-squares fitting of MN velocity estimates derived from all Tx-Rx angle pairs. In Stage 1, for each of the MN slow-time ensembles (matrix notation $x_{mn}$), multi-level sub-sampling is first performed to attain finer slow-time resolution. For this set of sub-sampled ensembles constructed for $x_{mn}$, three steps are performed: (i) clutter filter (to suppress tissue echoes); (ii) velocity estimation (based on lag-one autocorrelation: the classical CFI estimator); (iii) aliasing correction. After that, the sub-sampled ensembles are averaged to arrive at the mean flow estimate for that Tx-Rx angle pair. After doing the same for all angle pairs, MN raw velocity values (matrix notation u) would become available. In Stage 2, a flow vector $v=(v_x, v_z)$ is derived from u as follows. First, based on cross-beam Doppler principles[2], an MN×2 angle matrix A is formed from all MN Tx-Rx angle combinations. It is known that u=Av. Hence, v is computed by carrying out the least-squares fitting operation Au.

3. Dynamic Visualization:

For the v estimate of each pixel, a single-hue, color-coded arrow is formed. For high velocity magnitude, its corresponding arrow would be brighter in color and longer in length. Arrows for different VPI frames are compiled, and they are displayed as moving projectiles to enable quantitative visualization.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other objects and advantage of the present invention will become more apparent upon reference to the following specification and annexed drawings in which:

FIGS. 4A, 4B and 4C illustrate a set up for an anthropomorphic carotid bifurcation phantom study and an image of the co-planar geometry of a carotid bifurcation of a healthy and a diseased patient, respectively;

FIGS. 6A, 6B, 6C and 6D are still frame renderings according to the present invention showing the formation and dissipation of flow disturbance in a healthy carotid bifurcation phantom at (a) peak systole; (b) end of post-systolic down stroke; (c) dicrotic wave peak; and (d) end of dicrotic wave, while

FIGS. 7A, 7B, 7C, and 7D illustrate spatiotemporal differences in the two post-stenotic flow recirculation zones in the carotid bifurcation phantom with 50% ICA eccentric stenosis at: (a) peak systole; (b) arrival of post-systolic jet front at ICA distal end; (c) dicrotic wave peak; and (d) arrival of post-dicrotic jet front at ICA distal end, while

FIGS. 8A and 8B illustrate differences in the spatial-peak size of flow recirculation zones observed (a) after the systole and (b) after the dicrotic wave in the carotid bulb of the healthy bifurcation phantom, while

FIGS. 9A and 9B show flow recirculation zones in the 50%-stenosed bifurcation phantom during peak systole and dicrotic wave peak, with the relative time marked in two Doppler spectrograms in FIG. C while FIGS. 9D and 9E show the recirculation zone adjacent to the ICA inner wall during: (d) the systole; and (e) the dicrotic wave, while FIG. 9F shows the relative time marked in to Doppler spectrograms for two sample volumes placed at the proximal and distal ends of the ICA inner wall;

DETAILED DESCRIPTION OF THE INVENTION

Figure 10:
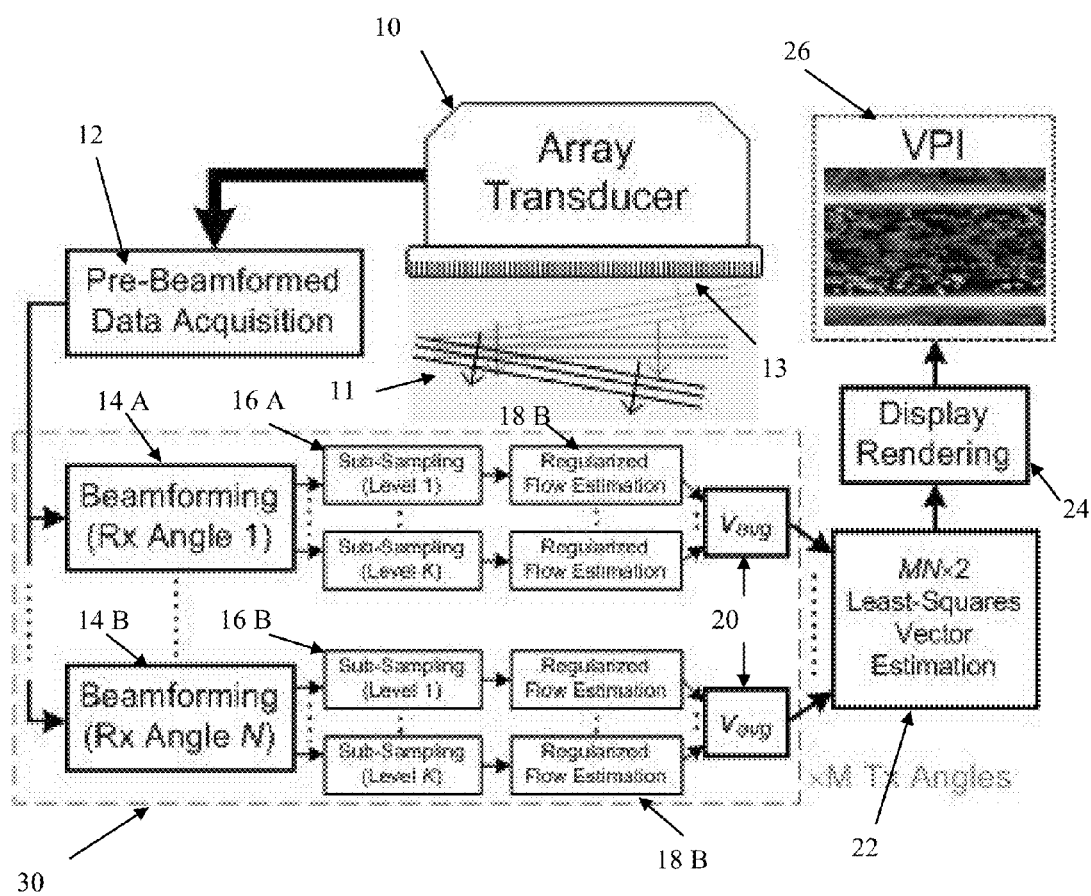
FIG. 10 is a system-level schematic of the stages involved in VPI according to the present invention.

An arrangement of apparatus for carrying out the vector projectile imaging (VPI) of the present invention is illustrated in FIG. 10. This arrangement carries out the steps of (1) data acquisition, (2) regularized flow vector estimation (including a first stage of multi-level sub-sampling and a second stage of flow vector derivation) and (3) dynamic visualization.

To achieve data acquisition an ultrasonic array transducer 10 is positioned on the outside of the patient's body adjacent the vasculature in which the fluid (e.g., blood) is to be imaged. The array 10 transmits a series of ultrasonic unfocused, steered plane waves 11 into the tissue at a high rate. The transmission angle with respect to the transducer surface 13 is changed after each wave. The transducer 10 also receives the waves reflected from the tissue at different receive steering angles and stores it in Pre-beam-Formed Data Acquisition device 12. This data is in the form of frames for each angle.

Each received frame of data is applied to a separate Beam Former 30 (enclosed in dotted lines), which includes Beam-Forming circuits $14_1$ to $14_N$. The output of each beam forming circuit is sub-sampled in Sub-Sampling circuits $16_1$ to $16_K$ for levels 1 through K. In turn, the output of each sub-sampling circuit is processed in a Regularized Flow Estimation circuit 18. Then the outputs of the flow estimation circuits for a frame are averaged in circuits 20.

A Least Squares Vector Estimation circuit 22 performs two major processing stages, i.e., (i) regularizing of the frequency shift estimation on each frame and; (ii) axial-lateral vector component estimation based on least-squares fitting. This circuit uses a customized estimation algorithm with post-hoc data regularization. In Display Rendering circuit 24 a duplex visualization method is used in which the primary channel shows color-encoded particle projectiles (little arrows) whose color code and length are both related to the velocity magnitude at a particular location in the imaged vasculature. The direction of the projectiles shows flow direction. The position of these projectiles is dynamically updated between frames to quantitatively highlight flow paths together with changes in magnitude and orientation. The secondary visualization channel depicts grayscale flow speckles that are derived based on the slow-time filter power. This supplementary flow information serves as an adjunct depiction of flow trajectories. The output of circuit 24 is the VPI image 26

Data Acquisition

Figure 1A:
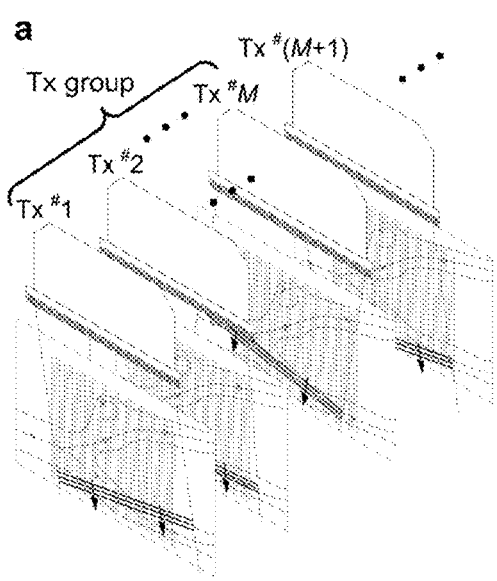
FIGS. 1A and 1B illustrate data acquisition in practicing the present invention based upon the use of plane wave transmissions and parallel beam-forming (both performed from multiple angles)
Figure 1B:
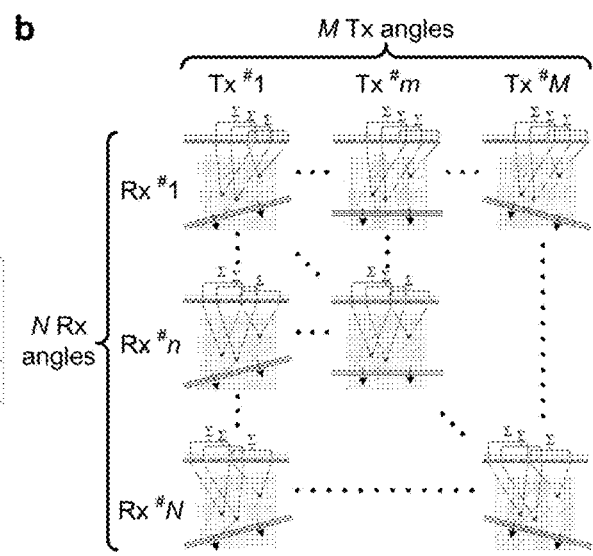

Data acquisition in VPI is based upon the use of plane wave transmissions and parallel beam-forming (both performed from multiple angles). As shown in FIG. 1A, on transmission (Tx), M plane wave pulsing events 11 are fired in sequence, and they each have a different steering angle. This group of firings is repeatedly executed to facilitate slow-time data acquisition. As shown in FIG. 1B, on reception (Rx), parallel beam-forming of N data frames, each with a different steering angle, is carried out for every plane wave pulsing event. The same pulsing sequence comprises MN Tx-Rx angle pairs.

Using a VPI framework, acquisition of flow vector information at high frame rates is facilitated by performing steered plane wave transmissions whose operating principles have recently matured for ultrasound imaging applications. See, Montaldo G, Tanter M, Bercoff J, Benech N, Fink M., "Coherent plane-wave compounding for very high frame rate ultrasonography and transient elastography," *IEEE Trans. Ultrason. Ferroelec. Freq. Contr.*, (2009), 56: 489-506, which is incorporated herein in its entirety. As shown in FIG. 1A, the firing sequence comprises a group of M broad-view unfocused pulsing events that are transmitted in order. Between adjacent firings, the transmission (Tx) steering angle (i.e. the propagation angle with respect to the transducer surface normal 13) is incrementally changed so as to cover a span of M angles over the entire group of pulsing events. This data acquisition scheme can be considered as the generalized form of the two-angle plane-wave firing strategy that has been applied to vector flow estimation (Ekroll et al. 2013 cited above). The merit of using more than two Tx angles is that flow vectors can be robustly estimated by solving an over-determined system of linear equations based on least-squares fitting principles. For a sequence with M Tx angles and pulse repetition frequency $f_{PRF}$, the nominal data acquisition frame rate ($f_{DAQ}$) (i.e. rate at which one group of firings can be executed) is in effect equal to $f_{PRF}/M$. Since $f_{PRF}$ is typically in the kHz range in ultrasound imaging, $f_{DAQ}$ can be well beyond the video display range as long as the number of Tx angles is kept small.

For each plane wave transmission at a given Tx angle, a set of N beam-formed data frames is generated in parallel based on the corresponding array of channel-domain pulse echoes (waves reflected from the tissue) which are acquired from the transducer 10 at the Pre-Beam Forming Data Acquisition Device 12. As illustrated in FIG. 1B, each frame is formed with a different receive (Rx) steering angle. The beam-formed data value of individual pixel positions in the frame is computed by leveraging well-established dynamic receive focusing principles that can be executed at real-time throughputs using parallel computing solutions. See, Yiu B Y S, Tsang I K H, Yu A C H, "GPU-based beam former: fast realization of synthetic aperture imaging and plane wave compounding," *IEEE Trans. Ultrason. Ferroelec. Freq. Contr.*, (2011), 58: 1698-1705, which is incorporated herein in its entirety? In general, with M unique Tx angles, beam-formed data frames are derived for MN combinations of Tx-Rx angle pairs (see FIG. 1B). The main rationale for using multiple Rx angles is that such a strategy would effectively increase the total number of independent frequency shift estimates (MN instead of M) available for vector flow estimation. The robustness of the least-squares vector estimation procedure can then be further enhanced, and in turn, more consistent flow vector estimates can be derived (to be discussed in the following subsections).

In order to monitor temporal changes in flow dynamics, plane wave transmission and receive beam-forming are carried out multiple times for all MN Tx-Rx angle pairs (as indicated in FIG. 1A). This process is essentially the same as performing slow-time sampling in single-gate pulsed Doppler ultrasound as disclosed in Evans D H, McDicken W N. *Doppler Ultrasound: Physics, Instrumentation and Signal Processing*. $2^{nd}$ Ed. New York: Wiley, (2000), which is incorporated herein in its entirety. As such, at every pixel position, there are MN (one for each Tx-Rx angle pair) slow-time ensembles of beam-formed samples available for flow vector estimation. For all ensembles, the slow-time sampling rate is simply equivalent to $f_{DAQ}$ (i.e. repetition rate for one group of Tx pulsing events), which in turn is equal to $f_{PRF}/M$ as described in Bercoff J, Montaldo G, Loupas T, Savery D, Meziere F, Fink M, Tanter M., "Ultrafast compound Doppler imaging: providing full blood flow characterization," *IEEE Trans. Ultrason. Ferroelec. Freq. Contr.*, (2011), 58: 134-147, which is incorporated herein by reference in its entirety. In turn, the slow-time aliasing limit, which equals 2$f_{DAQ}$ according to the Nyquist theorem, is given by 2$f_{PRF}/M$. In cases where a higher slow-time aliasing limit is needed to facilitate tracking of faster flow velocities, the number of Tx angles should be kept small; as well, a higher $f_{PRF}$ should be used as long as it satisfies the maximum imaging depth limit, which is after all governed by the pulse-echo sensing relation zmax 5 co/2$f_{PRF}$ (Evans and McDicken 2000 cited above).

Flow Vector Estimation

At each slow-time instant, the VPI method of the present invention performs flow vector estimation independently at all pixel positions based on their corresponding set of MN slow-time ensembles.

Figure 2A:
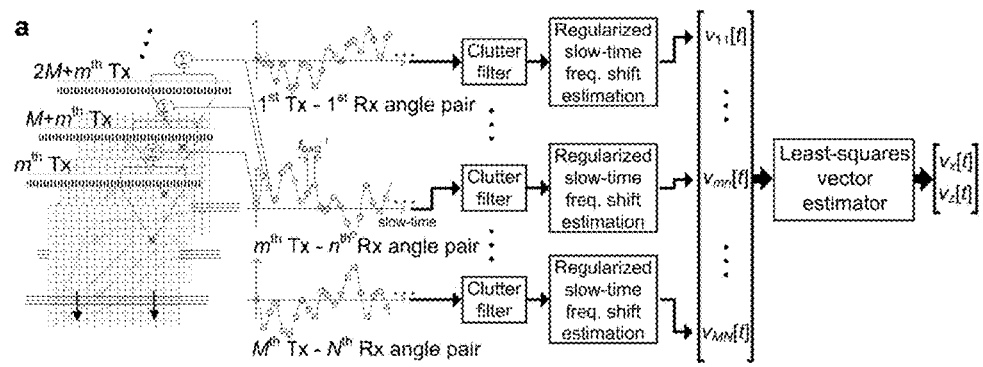
FIGS. 2A and 2B illustrates an arrangement for flow vector estimation according to the present invention for every pixel position and its corresponding set of slow-time signals from all Tx-Rx angle pairs.
Figure 2B:
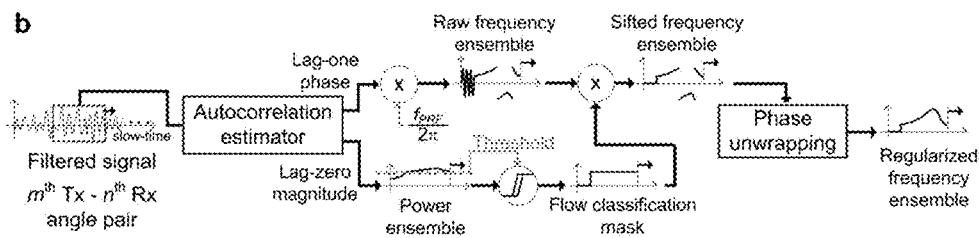

Flow vector estimation in VPI works by processing, for every pixel position, its corresponding set of slow-time signals from all Tx-Rx angle pairs. FIG. 2A illustrates clutter filtering and frequency shift estimation performed individually on each Tx-Rx angle pair in order to calculate the flow vector ($v_x[t]$, $v_z[t]$). Least-squares fitting is then performed with the set of frequency shift estimates $\{v_{mn}[t]\}$ as data input. FIG. 2B illustrates that for the $m^{th}$ Tx angle and $n^{th}$ Rx angle, regularized frequency shift estimation involves: autocorrelation computations over a slow-time sliding window (lag-one phase and lag-zero magnitude used respectively for frequency and power calculation), flow region masking based on determining the power threshold, and phase unwrapping.

As illustrated in FIG. 2A, clutter filtering with filters 30 is first applied individually to each slow-time ensemble to suppress unwanted tissue echoes or reflections of the transmitted signal. Subsequently, two major processing stages are carried out: (i) regularized slow-time frequency shift estimation on each of the MN filtered ensembles is carried out in the estimation circuits 32; and (ii) axial-lateral vector component estimation based on least-squares fitting of the MN frequency shift estimates that correspond to different Tx-Rx angle pairs is carried out in Least-Squares Vector Estimator 22 (shown in FIG. 10). The specific operations of each processing stage are described as follows.

To obtain consistent slow-time frequency shift estimates as necessary for accurate vector computation, a customized estimation algorithm with post-hoc data regularization is devised to individually process every filtered slow-time ensemble. As shown in FIG. 2B, the algorithm begins by calculating the mean signal frequency at various slow-time instants through the use of a sliding window strategy. For this step, a slow-time data window (centered about a given time of interest) is first defined over a filtered ensemble, and then the mean frequency over the windowed segment is computed using the well-established lag-one autocorrelation phase algorithm in estimator 36. See, Evans 2010 cited above, which is incorporated herein in its entirety. To facilitate flow region detection and adjunct rendering of flow speckles, the mean filtered power over the slow-time window is also calculated in parallel by finding the lag-zero autocorrelation magnitude. This estimation process is repeated at other slow-time instants by simply repositioning the window at the new time of interest. In turn, ensembles of slow-time frequency and power estimates are derived for each of the MN Tx-Rx angle pairs.

Following the estimation steps, a two-stage post-hoc processing strategy is performed to regularize entries of the slow-time frequency estimate ensembles. First, to remove spurious estimates at time instants where flow is not detected by a Tx-Rx angle pair, entries in the slow-time frequency ensembles are set to zero if their respective slow-time power estimate at that instant is below a predefined threshold (i.e. a flow classification mask 38 is applied similar to the color gain mask in color flow imaging). Second, akin to previous efforts in color flow signal processing, phase unwrapping is applied to the sifted slow-time frequency estimates to account for possible aliasing artifacts that may well occur when performing the lag-one autocorrelation algorithm. See, Lai X, Torp H, Kristoffersen K, "An extended autocorrelation method for estimation of blood velocity," *IEEE Trans. Ultrason. Ferroelec. Freq. Contr.*, (1997), 44: 1332-1342, which is incorporated herein in its entirety. This step effectively extends the dynamic range of the slow-time frequency estimates beyond the Nyquist sampling limit. Note that both regularization steps are performed individually on all MN ensembles of slow-time frequency estimates.

Least-Squares Vector Computation Algorithm

Once the MN slow-time frequency shifts are estimated from all Tx-Rx angle pairs, the axial and lateral components of the flow vector are derived using multi-angle Doppler analysis principles. See, Dunmire et al. 2000 cited above, which is incorporated in its entirety. This computational task is equivalent to solving an over-determined system of equations whereby MN data values (i.e. frequency shift estimates from all the Tx-Rx angle pairs at one slow-time instant) are used as inputs to solve for two unknowns (i.e. axial velocity and lateral velocity). Specifically, the flow vector $v=(v_z, v_x)$ can be estimated through a least-squares fitting approach. The advantage of adopting this algebraic framework is that each resulting flow vector estimate would be optimized in the sense that its mean squared error is minimized for a given input. In turn, in cases with noisy data input, consistent estimation performance can still be maintained compared with the two-equation, two-unknown formulation that corresponds to the conventional two-angle vector Doppler method (Ekroll et al. 2013; Kripfgans et al. 2006 cited above).

In the least-squares vector computation method, v can be calculated by carrying out a matrix operation with each MN×1 measurement vector u (consisting of individual frequency shift values).

The least-squares flow vector estimator can be considered a generalized form of the cross-beam Doppler estimation method in which multiple Tx-Rx angle pairs are used in lieu of the two-angle approach that has been reported previously. See, Kripfgans et al. 2006; Tortoli et al. 2006, 2010; and Ekroll et al. 2013, all cited above and incorporated herein in their entirety. In the case with MN combinations of Tx-Rx angle pairs, the $m^{th}$ Tx angle can be denoted as $\theta_m$ and the $n^{th}$ Rx angle can be denoted as $\varphi_n$. Note that, since plane wave transmissions and dynamic receive focusing are used, $\theta_m$ and $\varphi_n$ would remain the same for all pixels within the imaging view. It is well-known from the Doppler equation that, with this angle pair configuration, the slow-time frequency shift $\varphi_{mn}$ for an object moving at velocity magnitude v and angle $\alpha$ is equal to:

$$\phi_{mn} = \frac{v\cos(\theta_m - \alpha) + v\cos(\varphi_n - \alpha)}{c_o} f_o, \quad (1)$$

where $c_o$ is the acoustic speed and $f_o$ is the ultrasound center frequency. See, Dunmire et al. 2000, cited above and incorporated herein in its entirety. Following similar derivations, the mathematical form expressed in (A1) can be modified by noting two points: (i) there exists a trigonometry relation [cos(A−B)=cos(A)cos(B)+sin(A)sin(B)]; and (ii) the axial and lateral velocity components are respectively equal to $v_z=v\cos(\alpha)$ and $v_x=v\sin(\alpha)$. See, Tsang I K H, Yiu B Y S, Yu A C H, "A least-squares vector flow estimator for synthetic aperture imaging," *Proc. IEEE Ultrason. Symp.*, (2009), 1387-1390, which is incorporated herein in its entirety. Substituting these relations into (A1), the following revised form of the Doppler equation can be obtained:

$$v_z(\cos\theta_m + \cos\varphi_n) + v_x(\sin\theta_m + \sin\varphi_n) = \frac{c_o}{f_o}\phi_{mn}. \quad (2)$$

The flow vector estimator seeks to solve for $v_x$ and $v_z$, the two unknowns in (A2), by forming an over-determined system of equations from MN realizations of (A2) as made available through the use of different Tx-Rx angle pairs. In matrix notation, this system of equations can be expressed in the following form for a given flow vector $v=(v_x, v_z)$:

$$Av = u \Rightarrow \begin{bmatrix} \cos\theta_1 + \cos\varphi_1 & \sin\theta_1 + \sin\varphi_1 \\ \vdots & \vdots \\ \cos\theta_M + \cos\varphi_N & \sin\theta_M + \sin\varphi_N \end{bmatrix} \begin{bmatrix} v_z \\ v_x \end{bmatrix} = \begin{bmatrix} u_{11} \\ \vdots \\ u_{MN} \end{bmatrix} \quad (3)$$

where A is the angle-pair matrix (MN×2 in size) and u as the measurement vector (MN×1 in size). Note that $u_{mn}$ is essentially equal to the right hand side of (A2) for a given Tx-Rx angle pair (i.e. $u_{mn}=c_o\varphi_{mn}/f_o$).

From linear algebra principles, it is well known that v in Equation (3) can be found by multiplying the pseudo-inverse of A with v: a solution that is often referred to as the least-squares fitting solution. See, Moon T K, Stirling W C, "*Mathematical Methods and Algorithms for Signal Processing*," Upper Saddle River: Prentice-Hall, (2000), which is incorporated herein in its entirety. Thus, with each MN×1 measurement vector u (consisting of individual frequency shift values), v can be calculated by carrying out the following matrix operation:

$$v = \begin{bmatrix} v_z \\ v_x \end{bmatrix} = (A^T A)^{-1} A^T u \qquad (4)$$

where the T superscript denotes a matrix transpose operation and entity $(A^T A)^{-1} A^T$ is well-known in linear algebra as the pseudo-inverse of matrix A. See Moon T K, Stirling W C, "*Mathematical Methods and Algorithms for Signal Processing*," Upper Saddle River: Prentice-Hall, (2000), which is incorporated herein in its entirety. Note that the pseudo-inverse $(A^T A)^{-1} A^T$ is essentially a 2×MN matrix of constant values (as long as the Tx-Rx angle pairs remain the same). Thus, the same pseudo-inverse is applicable to different pixel positions. It is also worth pointing out that, for the least-squares estimator given in Equation (4), the resulting flow vector estimate can be considered as an optimal solution in the sense that its mean-squared error is minimized for a given input. It is worth emphasizing that Equation (4) is carried out individually at every pixel position and at each slow-time instant.

Dynamic Visualization Procedure

Using the computation protocol according to the present invention, frames of flow vector information can be generated at a rate of $f_{VPI}$, which equals to $f_{DAQ}/K$ [i.e. $f_{PRF}/(MK)$] for a step size of K slow-time samples when executing the sliding window implementation. To facilitate dynamic rendering of these flow vector estimates, a novel duplex visualization method is used. Its primary visualization channel shows color-encoded particle projectiles (small arrows) whose color code and projectile length are both related to the velocity magnitude (on a scale from zero to a tunable maximum value). The direction of the projectiles shows flow direction. The position of these projectiles is dynamically updated between frames to quantitatively highlight flow paths together with changes in magnitude and orientation. The secondary visualization channel depicts grayscale flow speckles that are derived based on the slow-time filter power. This supplementary flow information serves as an adjunct depiction of flow trajectories in ways similar to that offered by the B-flow imaging technique. See, Chiao R Y, Mo L Y, Hall A L, Miller S C, Thomenius K E, "B-mode blood flow (B-flow) imaging," *In: Proceedings, IEEE Ultrasonics Symposium*, San Juan, Puerto Rico, 22-25 October. New York: IEEE; (2000), p. 1469-1472; and Lovstakken L, Bjaerum S, Martens D, Torp H, "Blood flow imaging—A new real-time, 2-D flow imaging technique," *IEEE Trans Ultrason Ferroelectr Freq Control* (2006), 53:289-299. Note that the graphical representation of multidirectional flow dynamics rendered by our duplex visualization approach is essentially different from the dot-based particle visualization algorithm that has been reported recently in ultrasound flow imaging (Flynn et al. 2011).

Figure 3A:
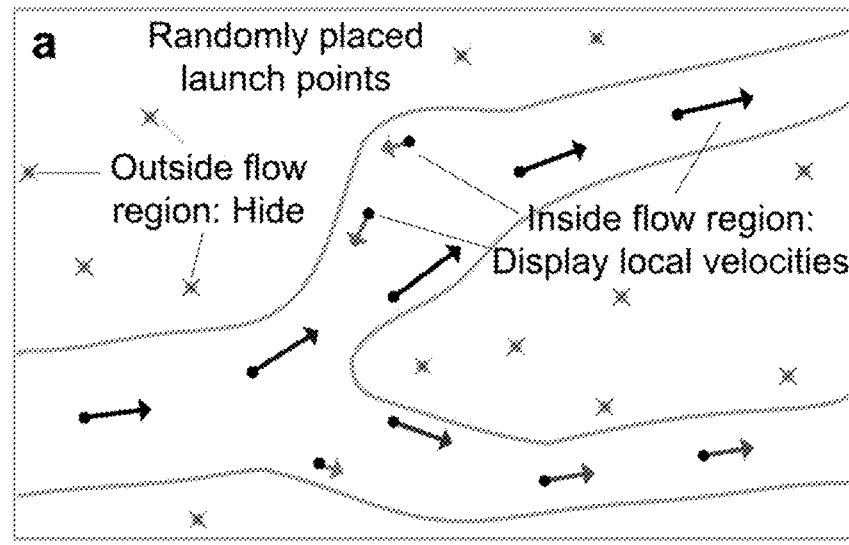
FIGS. 3A and 3B are quantitative flow visualizations according to the present invention utilizing dynamic rendering of color-encoded particle projectiles.
Figure 3B:
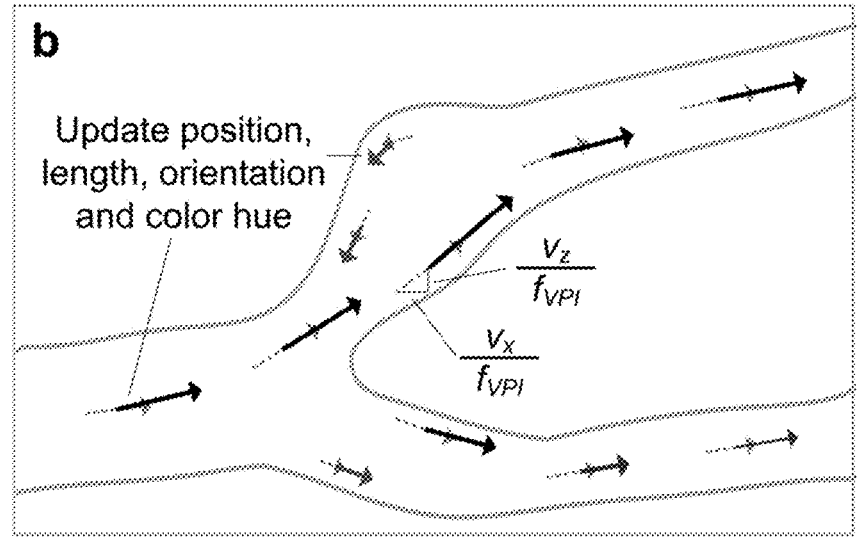

VPI provides quantitative flow visualization through dynamic rendering of color-encoded particle projectiles. In FIG. 3A set of pixels in the image view is first designated as projectile launch points. Those outside the flow region (identified based on power thresholds) are hidden. Projectile length and color hue are set based on velocity magnitude. FIG. 3B shows the projectile position updated by calculating its inter-frame displacement based on the velocity vector estimate.

The dynamic projectile method of the VPI visualization protocol works as follows: First, as shown in FIG. 3A, at the start of the loop, a random set of pixels in the imaging view are chosen as launch points, and their respective color-encoded projectiles are displayed. Subsequently, to update each projectile's position in the next frame, three steps are executed in sequence as shown in FIG. 3B: (i) calculating the incremental 2-D displacement by multiplying between the projectile's corresponding axial-lateral velocities and the inter-frame period (i.e. reciprocal of $f_{VPI}$); (ii) updating the projectile's position in the new frame based on the calculated displacement (discretized to the nearest pixel in the image grid); and (iii) displaying the color-encoded projectile of the new frame at the updated position. This process is essentially similar to algorithms proposed in the computer graphics field and is repeated for a given projectile lifetime (randomized in terms of the number of frames), and afterward the entire dynamic visualization loop is restarted by regenerating new projectiles at the launch points (based on vector estimates at the new slow-time instant). See, McLoughlin T, Laramee R S, Peikert R, Post F H, Chen M, "Over two decades of integration-based, geometric flow visualization," *Computer Graphics Forum* 2010; 29:1807-1829. Note that, to suppress spurious projectiles, a display gain strategy is adopted as similar to that used in color flow imaging. In particular, a projectile would be displayed only if its instantaneous pixel position falls within the flow region, as identified based on the slow-time filtered power map (i.e. pixels with power greater than a given threshold are classified as flow region). Otherwise, a new projectile would be regenerated at the original launch point.

Hardware and Parameters

The VPI invention has been implemented using a research-purpose, channel-domain imaging platform that allows the transmission and reception operations of each array element to be configured individually. This platform is a composite system in which the front-end of a SonixTouch research scanner (Ultrasonix, Richmond, BC, Canada) was coupled to a pre-beam-formed data acquisition tool, and data was streamed to a back-end computing workstation through a universal serial bus link (specifications listed in Table 1a). An L14-5 linear array (Ultrasonix) was used as the operating transducer. See, Cheung C C P, Yu A C H, Salimi N, Yiu B Y S, Tsang I K H, Kirby B, Azar R Z, Dickie K, "Multi-channel pre-beamform data acquisition system for research on advanced ultrasound imaging methods," *IEEE Trans. Ultrason. Ferroelec. Freq. Contr.*, (2012) 59: 243-253, which is incorporated herein in its entirety.

Pressure field recordings of this ultrasound transmission hardware were taken using a membrane hydrophone (HMB-0500, Onda, Sunnyvale, Calif., USA) that was mounted on a three-axis micro-positioner (ASTS-01, Onda). When operating in plane wave excitation mode, our scanner hardware generated a derated peak negative pressure of 0.72 MPa (located at 2-cm depth). This pressure value, for our given pulsing parameters, corresponded to a mechanical index of 0.32; spatial-peak, temporal-average intensity of 0.16 W/cm2; and spatial-peak, temporal-peak intensity of 27 W/cm2 (assuming operation in 37_C degassed water). These numbers were well within the safety limits defined by the U.S. Food and Drugs Administration. See Duck F A, "Medical and non-medical protection standards for ultrasound and infrasound," *Prog Biophys Mol Biol* (2007) 93:176-191.

A vector estimation configuration with three Tx angles (−10°, 0°, +10°) and three Rx angles (−10°, 0°, +10°) was implemented (i.e. M=3, N=3, MN=9). To realize such a configuration, a steered plane wave pulsing sequence was programmed on the platform by executing relevant functions in the TEXO software development kit (Ultrasonix) to define array channel delays that only generate angle steering without focusing. Typical pulse-echo imaging parameters were used as summarized in Table 1b, and pre-beam-formed channel-domain data was acquired on reception.

TABLE 1

Parameters Used for Experimental Realization of VPI

| Parameter | Value |
| --- | --- |
| (a) Imaging Platform | |
| Number of Tx/Rx Channels | 128 |
| Array Pitch | 0.3048 mm |
| Pre-Beam formed Data Sampling Rate | 40 MHz |
| Pre-Beam formed Data Bit Resolution | 12 |
| (b) Data Acquisition | |
| Imaging Frequency | 5 MHz |
| Tx Pulse Duration | 3 cycles (0.6 μs) |
| Pulse Repetition Frequency | 10 kHz |
| Effective Data Acquisition Rate | 3.33 kHz |
| Maximum Imaging Depth | 2 cm |
| Data Acquisition Duration | 1 s |
| (c) Beam Forming | |
| Pre-Beam-formed Data Filter Pass band | 3-7 MHz |
| Filter Design Method | Equiripple |
| Data Frame Size | 200 × 380 pixels |
| Pixel Dimension | 0.1 × 0.1 mm |
| (d) Slow-time data processing | |
| Normalized clutter filter cutoff | 0.05 |
| Sliding Window for flow estimation | 128 samples |
| Sliding Window Step Size | 8 samples |
| (d) VPI Visualization | |
| Nominal Frame Rate | 416 fps |
| Launch Point Density | 4% |
| Mean Projectile Lifetime | 30 frames |
| Flow Speckle Dynamic Range | 40 dB |

TABLE 2

Alternative Experimental Parameters

| Parameter | Value |
| --- | --- |
| Imaging Specifications | |
| Imaging frequency | 5 MHz |
| # of array channels | 128 |
| Pulse duration | 3 cycles (0.429 μs) |
| Pulse repetition frequency | 10 kHz |
| Tx-Rx steering angles | −10°, 0°, +10° |
| Flow Pattern Specifications | |
| Peak inlet flow rate | 6 ml/s |
| Pulse cycle frequency | 1.2 Hz |

Figures 11A, 11B:
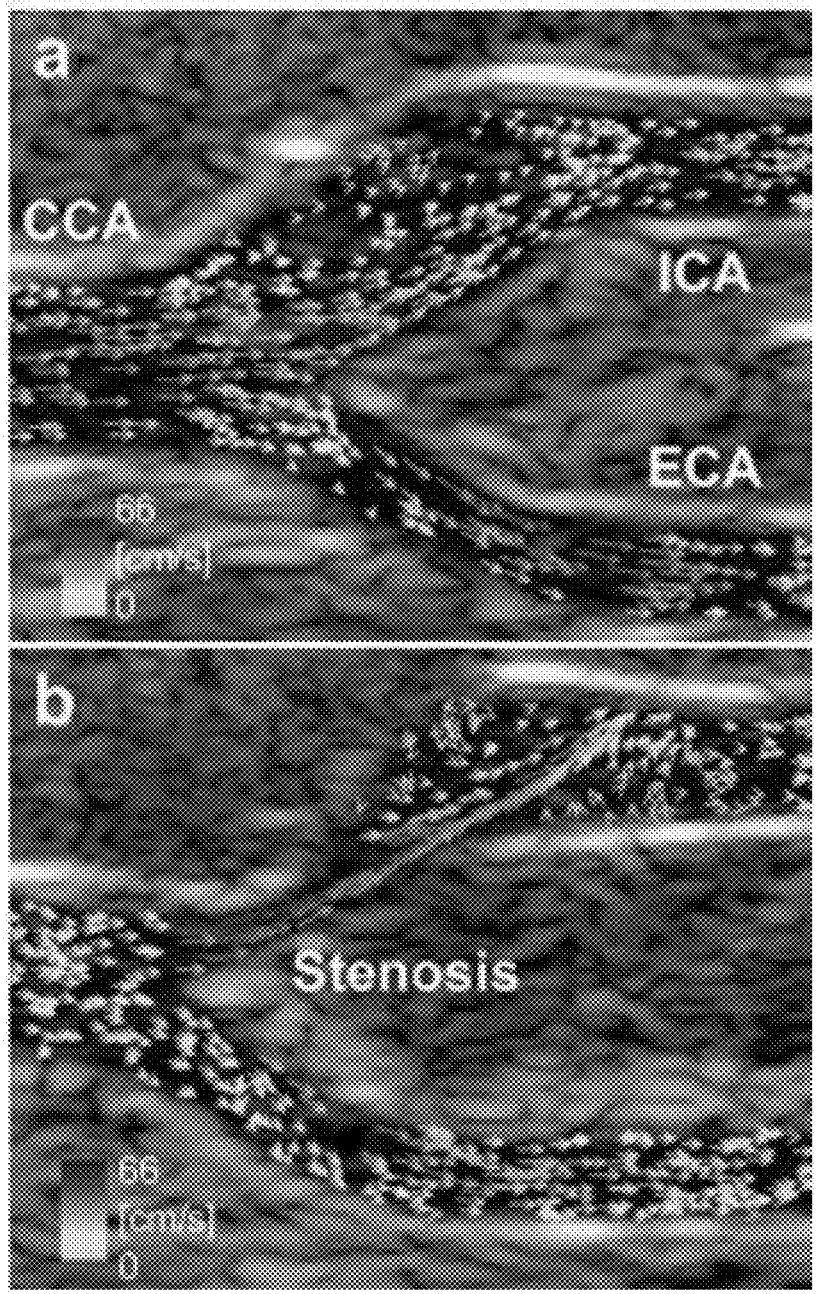
FIGS. 11A and 11B are images of examples of VPI taken at peak systole for two carotid bifurcation models: (a) healthy and (b) with 50% eccentric stenosis at the entrance to ICA.
Figure 12A:
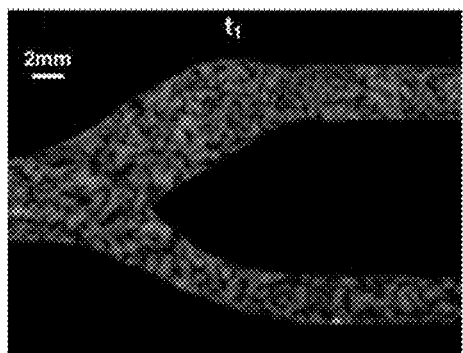
FIGS. 12A, 12B, 12C, and 12D are still frame renderings according to the present invention showing only in gray scale speckles the formation and dissipation of flow disturbance in a healthy carotid bifurcation phantom at (a) peak systole; (b) end of post-systolic down stroke; (c) dicrotic wave peak; and (d) end of dicrotic wave.
Figure 12B:
Figure 12C:
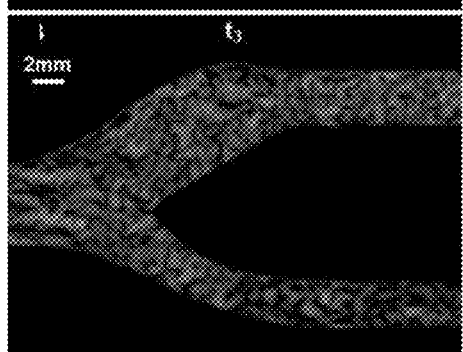
Figure 12D:
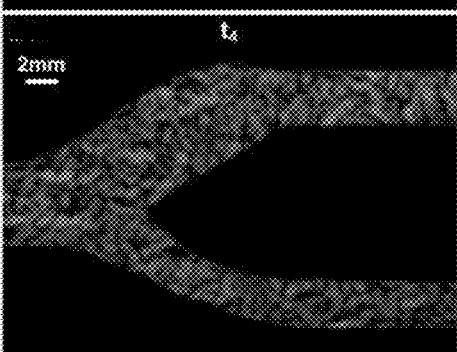
Figure 13A:
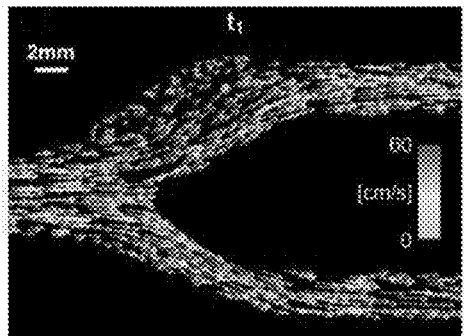
FIGS. 13A, 13B, 13C, AND 13D are still frame renderings according to the present invention showing only projectiles in the formation and dissipation of flow disturbance in a healthy carotid bifurcation phantom at (a) peak systole; (b) end of post-systolic down stroke; (c) dicrotic wave peak; and (d) end of dicrotic wave.
Figure 13B:
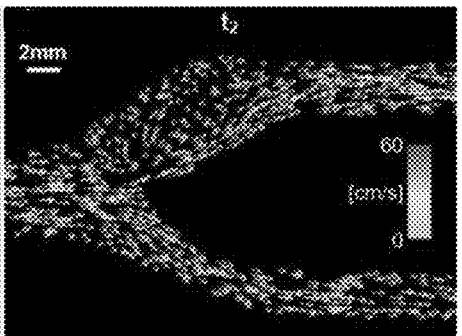
Figure 13C:
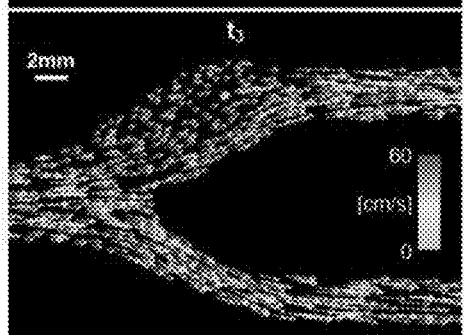
Figure 13D:
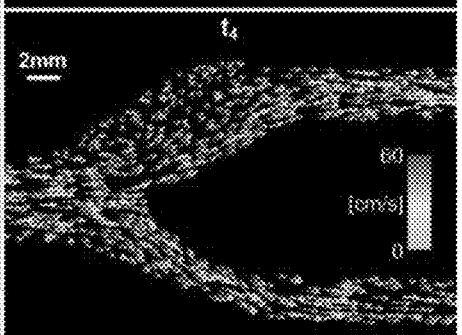

A 3-Tx, 3-Rx VPI configuration was implemented. Also, for each Tx-Rx angle pair, a 3-level sub-sampling was imposed during flow estimation. VPI was tested on anatomically realistic flow models that resembled healthy and stenosed carotid bifurcation. These are suitable geometries because flow dynamics within them are known to be multi-directional and significantly time-varying. The phantoms are wall-less designs based on lost-core casting with polyvinyl alcohol gel. Pulsatile flow is supplied through the use of a gear pump with programmable flow rates. The resulting images are shown in FIG. 11. In FIG. 11, the images are of VPI taken at peak systole for two carotid bifurcation models: FIG. 11A healthy and FIG. 11B with 50% eccentric stenosis at the entrance to ICA. This shows examples of VPI in rendering long-axis views of two bifurcation models. The results at peak systole are shown. In the healthy case, VPI accurately projected the main transit path of blood flow. In the stenosis case, VPI quantitatively highlighted the high velocity jet emerging at the stenosis site, curvy transit path downstream from the stenosis, and significant re-circulatory flow in the ICA bulb.

After streaming the acquired data offline to the back-end processor, various image formation and visualization operations were carried out as required for VPI. First, to improve the channel-domain signal-to-noise ratio, a finite-impulse-response band pass filter (minimum order; parameters listed in Table 1c) was applied to the pre-beam-formed data of each channel using Matlab (R2012a; Mathworks, Natick, Mass., USA). After that, delay-and-sum beam-forming from the three Rx angles were executed using a graphical processing unit (GPU) based parallel computing approach like that disclosed in Yiu et al. 2011, which was previously cited and is incorporated by reference in its entirety. Note that an array of two GTX-590 GPUs (NVidia, Santa Clara, Calif., USA) was used for this operation to facilitate processing at real-time throughput. Subsequently, an implementation for speckle imaging was used as disclosed in Yiu B Y S, Tsang I K H, Yu A C H, "GPU-based beam former: fast realization of synthetic aperture imaging and plane wave compounding," *IEEE Trans. Ultrason. Ferroelec. Freq. Contr.*, (2011), 58: 1698-1705. In addition, clutter filtering (in the form of a minimum order high-pass finite-impulse-response filter; see Table 1d for parameters) and lag-one autocorrelation were performed individually on the nine Tx-Rx angle pairs at each pixel position. Other downstream operations related to vector estimation (post-hoc regularization and least-squares fitting) were then conducted in Matlab. Ad hoc persistence and median filtering were also performed. At last, VPI image sets were obtained and rendered using the duplex dynamic visualization algorithm of the present invention and the parameters listed in Table 1d. Note that the flow information in our VPI image sets was overlaid on top of a background B-mode image frame that was formed from spatial compounding of the beam-formed data frames formed from the nine Tx-Rx angle pairs.

In order to evaluate the accuracy of the flow vector estimation algorithm used in our VPI technique, steady-flow calibration experiments were first conducted using a multi-vessel flow phantom that we fabricated in-house. The phantom comprised three wall-less straight tubes whose long axes were aligned along the same plane; each tube had a different diameter (2, 4 and 6 mm) and flow angle (−10°, 0° and +10°), and they were positioned at different depths (1.5, 4 and 6 cm). By use of an investment casting protocol similar to that described in our previous work (Yiu and Yu 2013, previously cited), the phantom was fabricated with polyvinyl alcohol cryogel as the tissue-mimicking material, whose acoustic attenuation coefficient and acoustic speed were respectively measured to be 0.24 dB/cm, MHz and 1518 m/s.

The phantom was connected to a gear pump (AccuFlow-Q, Shelley Medical Imaging, London, ON, Canada) that supplied continuous circulation of blood-mimicking fluid (Shelley; 1037 kg/m3 density, 3.95 3 106 m2/s viscosity) at a flow rate of 2.5 mL/s. The transducer scan plane was aligned to the long axis of the three vessels (which were expanded to diameters of 2.2, 4.4 and 6.3, respectively, because of flow-mediated dilation). Raw data were then acquired for the three-Tx, three-Rx configuration based on the parameters described above, and the lumen velocity profiles were estimated using VPI's flow vector computation algorithm. Results were correlated with the theoretical parabolic profiles, whose centerline velocities were 131, 31 and 16 cm/s, respectively, for the three dilated vessels To assess the practical efficacy of the VPI technique, this framework was used to image complex flow dynamics inside anatomically realistic carotid bifurcation phantoms. In particular, efficacy of VPI was evaluated through an anthropomorphic carotid bifurcation phantom study. FIG. 4A illustrates the experimental setup comprising the flow circuit and the imaging platform. Sample B-mode images are shown for two bifurcation models. In FIG. 4A a transmit pulse circuit 40 delivers its signal to the array transducer 10, which is the same or similar to the one shown in FIG. 10 and which may have, e.g., 128 TX/RX channels. It is triggered by a signal from channel domain data acquisition tool 48. The transducer causes ultrasonic waves to be applied to artificial tissue 42, which has a fluid flow path that branches. The fluid from the tissue mimic 42 passes from both branches into a fluid reservoir 44 where it is collected and returned to the tissue mimic via a pump 46. The return signal from the tissue mimic 42 is received by the array 10 and is delivered to the channel-domain data acquisition tool 48, which conditions it. Circuit 48 is similar to circuit 12 in FIG. 10. This conditioned signal is applied to Beam Former 30, which is the same or similar to circuit 30 in FIG. 10. Least squares vector estimation is performed in circuit 22 and the result is presented on display 26, again in a form similar to that in FIG. 10.

Figure 4B:
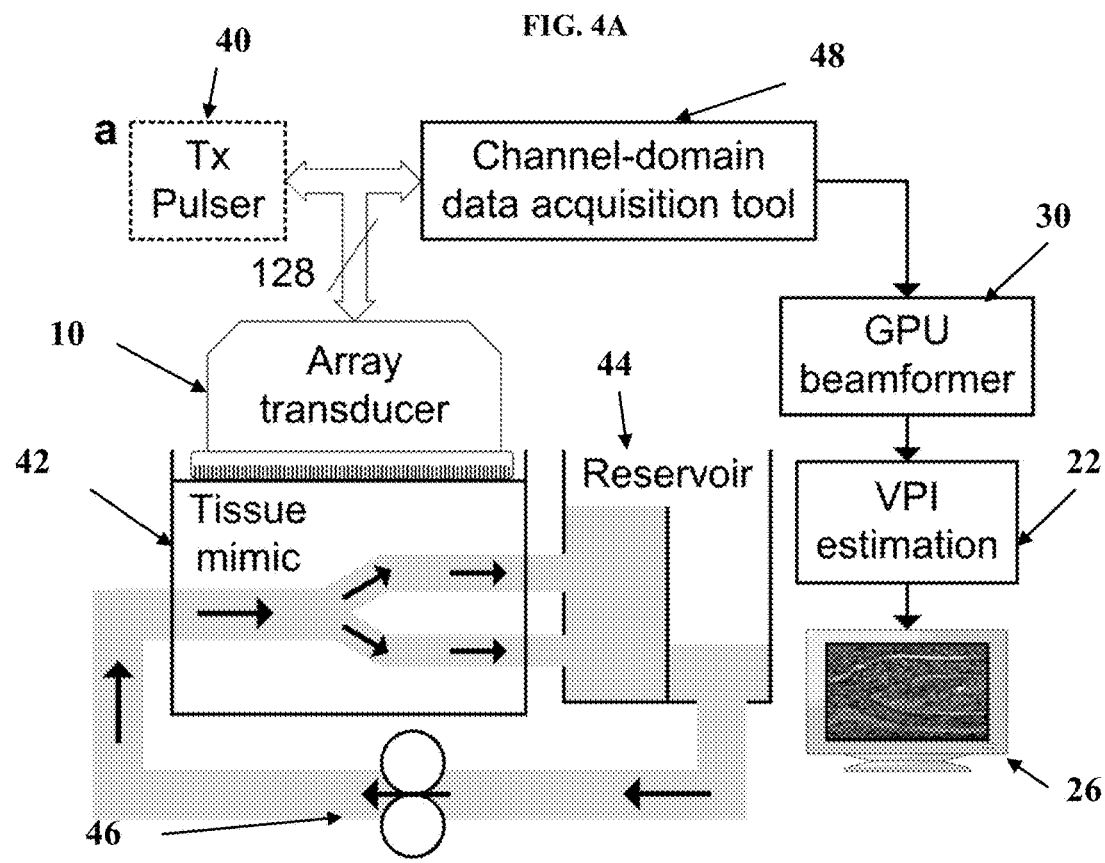
Figure 4C:
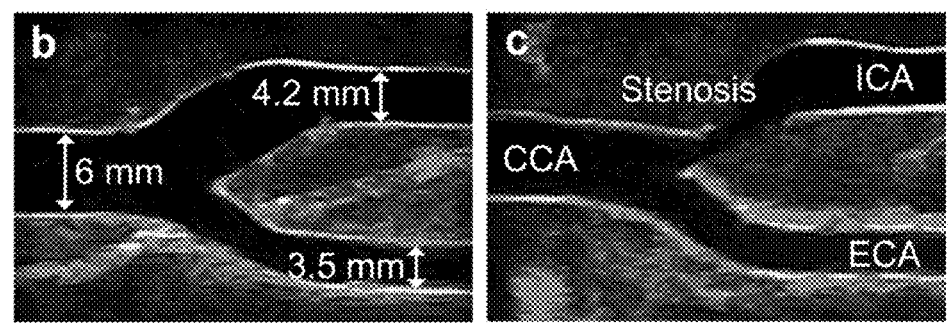

FIG. 4B shows the image for a healthy co-planar geometry and FIG. 4C shows the image for a diseased bifurcation with 50% eccentric stenosis at the ICA branch entrance. Vessel dimensions are as shown. (CCA=common carotid artery; ICA=internal carotid artery; ECA=external carotid artery).

Note that the carotid bifurcation vasculature is rather suitable for this investigation because it possessed curved vessel geometries in the vicinity of the junction between three branches: the common carotid artery (CCA), the internal carotid artery (ICA), and the external carotid artery (ECA). In other words, it effectively allowed testing of the ability of the three-Tx, three-Rx VPI configuration to track flow patterns with significant multi-directional and spatiotemporal variations. Another point of merit in using these geometries is that their flow dynamics have already been extensively characterized by others using optical particle image velocimetry (Kefayati S, Poepping T L "Transitional flow analysis in the carotid artery bifurcation by proper orthogonal decomposition and particle image velocimetry." *Med. Eng. Phys.,* 2013; 35: 898-909.; Poepping et al. (2010)) and computational fluid dynamics (Steinman D A, Poepping T L, Tambasco M, Rankin R N, Holdsworth D W, "Flow patterns at the stenosed carotid bifurcation: effect of concentric versus eccentric stenosis," *Ann. Biomed. Eng.,* 2000; 28: 415-423. This information effectively provides an established reference for comparison with the flow patterns rendered by VPI.

Two different carotid bifurcation phantom models were used for experimentation (i) healthy co-planar geometry (FIG. 4B) and (ii) diseased bifurcation with 50% eccentric stenosis at the ICA branch entrance (FIG. 4C). The phantoms were wall-less designs with polyvinyl alcohol cryogel as the tissue mimicking material, and they were fabricated using the same procedure as described. See, Yiu and Yu 2013 previously cited. The flow pulse, with a 72-bpm pulse rate (i.e., 1.2 Hz) and a 5 mL/s systolic flow rate, resembled a carotid pulse pattern that featured a primary systolic upstroke and a secondary dicrotic wave (predefined in the pump system). As explained elsewhere (Yiu and Yu 2013), these flow parameters would generally yield laminar flow conditions, and thus any complex flow patterns that arise can be ascribed to flow disturbance brought about by local tortuousness in the vessel geometry (rather than flow turbulence).

A steady-flow calibration experiment was first conducted by connecting the healthy bifurcation phantom to a gear pump (AccuFlow-Q; Shelley Medical Imaging, London, ON, Canada) that supplied continuous circulation of blood mimicking fluid (Shelley; 1037 kg/m$^3$ density, 3.95×10$^6$ m$^2$/s viscosity) at 5 ml/s flow rate. The transducer scan plane was aligned to the CCA long axis (expanded to 6.4 mm diameter due to flow-mediated dilation), and raw data was acquired for the three-Tx, three-Rx configuration based on the parameters described earlier. The lumen velocity profile was then estimated using VPI's flow vector computation algorithm. Results were compared to the theoretical parabolic profile (with 31 cm/s centreline velocity).

Next, pulsatile flow experiments were performed using the bifurcation phantoms. The flow pulse, with a 72 bpm pulse rate (i.e. 1.2 Hz) and a 5 ml/s systolic flow rate, resembled a carotid pulse pattern that featured a primary systolic upstroke and a secondary dicrotic wave (we-defined in the pump system). VPI cineloops were then generated by processing raw data acquired under such flow settings to determine the ability of VPI in visualizing complex flow features. To facilitate comparison, Doppler spectrograms were computed at representative pixel positions in the imaging view by reprocessing the raw slow-time ensembles at those places.

Figure 5A:
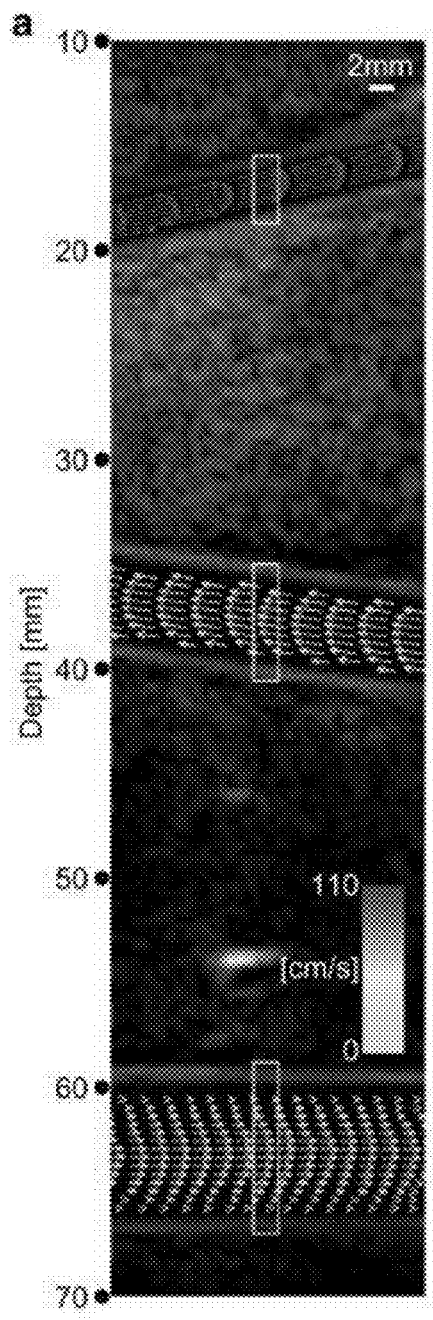
FIGS. 5A and 5B illustrate a color static map of estimated flow vectors and a graph of velocity versus position from the proximal wall of vessel for vessels at three different depths.
Figure 5B:
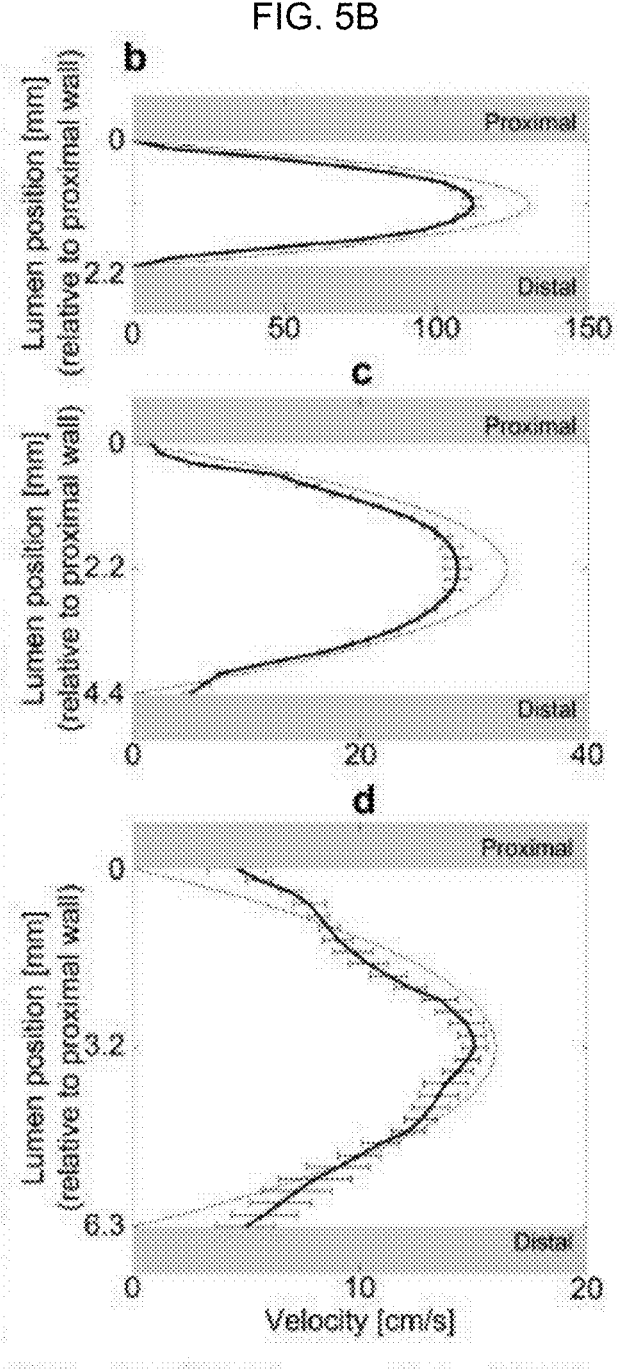

The vector computation algorithm of VPI was found to be capable of deriving flow vector estimates at high accuracy. Corresponding results obtained from the steady-flow calibration experiment are shown in FIG. 5. FIG. 5 shows the flow vector estimator of vector projectile imaging (VPI) (three-transmission [Tx], three-reception [Rx] configuration) derived consistent accurate flow estimates in a multi-vessel steady-flow calibration experiment (2.5 mL/s flow rate). FIG. 5A shows a static map of estimated flow vectors in three flow tubes positioned at different depths (1.5, 4, 6 cm), of different sizes (2, 4, 6 mm diameter) and oriented at different angles (−10°, 0°, +10°). The color code and length of each vector were related to the flow velocity magnitude. The scale is displayed in log form in view of the high velocity dynamic range). See FIGS. 5B, 5C, and 5D. For the three vessels, the estimated velocity magnitudes (solid lines) at different axial positions within the lumen closely match theory (dashed line). Results averaged from 50 lateral positions (error bars 5 standard deviations).

The plots are the flow vector profiles in the CCA of a healthy bifurcation phantom (with 5 ml/s constant flow rate) with the transducer placed in parallel with the CCA vessel. As can be observed in FIG. 5A, the angle orientation of the flow vectors within the lumen (visualized as static color-encoded projectiles) was generally accurate in that they consistently depicted the flow direction in this calibration flow scenario that comprised three vessels of different angles. The flow angle estimates remained robust at axial positions near the transducer (top vessel, centered at 1.5 cm depth) and away from the transducer (bottom vessel; centered at 6-cm depth).

The estimated flow speed magnitude across the lumen of the three vessels was generally found to resemble a parabolic shape that matched well with the theoretical prediction. As illustrated in FIGS. 5B, 5C, and 5D, for the top, middle and bottom vessels, the estimated centerline velocity magnitude was respectively 110.4, 28.6 and 15.1 cm/s (each based on average of 50 estimates). They were −16.1%, −9.1% and −6.2% different from the theoretical value. This offset is after all typical for mean velocity estimation, because each spatial point, being a finite-sized range gate, actually covered a range of velocities along the parabolic flow gradient, and in turn, the mean velocity estimate would correspond to the average over this depth range.

Calibration results showed that, using three transmit angles and three receive angles (−10°, 0°, +10° for both), VPI can accurately compute flow vectors even when the transducer was placed in parallel to the vessel (6.4 mm dilated diameter; 5 ml/s steady flow rate). The practical merit of VPI was further demonstrated through an anthropomorphic flow phantom investigation that considered both healthy and stenosed carotid bifurcation geometries. For the healthy bifurcation with 1.2 Hz carotid flow pulses, VPI was able to render multi-directional and spatiotemporally varying flow patterns (using 416 fps nominal frame rate, or 2.4 ms time resolution). In the case of stenosed bifurcation (50% eccentric narrowing), VPI enabled dynamic visualization of high-speed flow jet and recirculation zones.

Figure 6A:
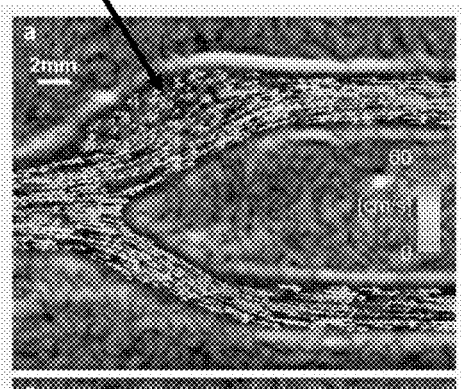
Figure 6B:
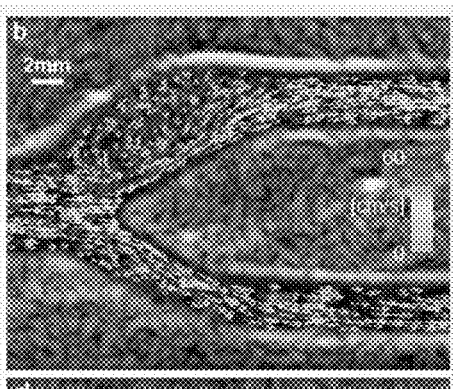
Figure 6C:
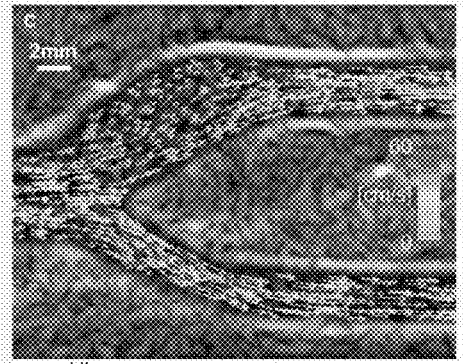
Figure 6D:
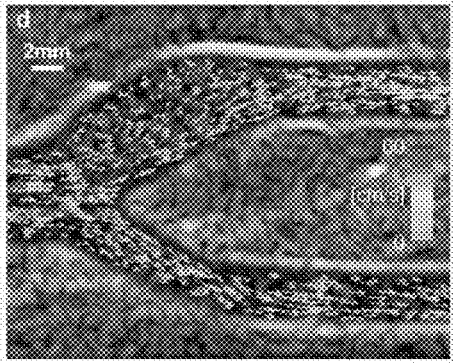
Figure 6E:
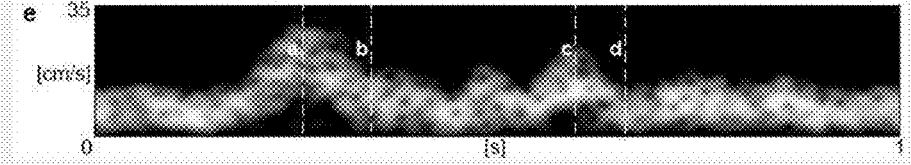
FIG. 6e shows the relative positions in the pulse cycle in a Doppler spectrogram.
Figure 7A:
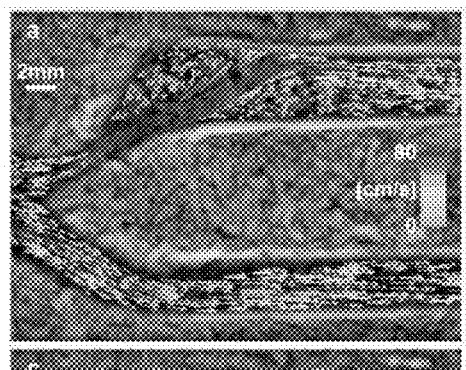
Figure 7B:
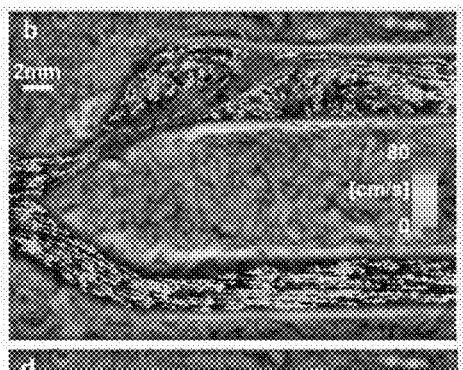
Figure 7C:
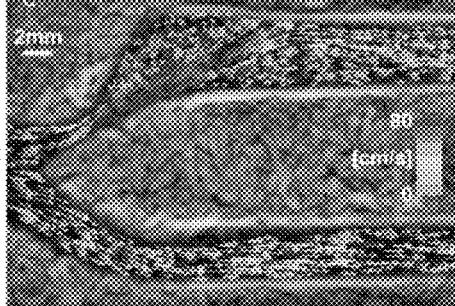
Figure 7D:
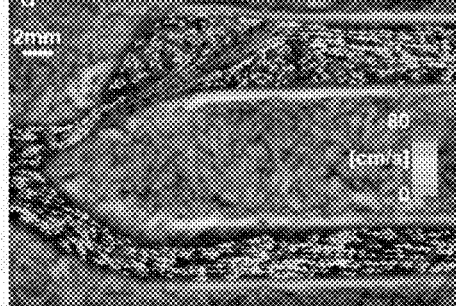
Figure 7E:
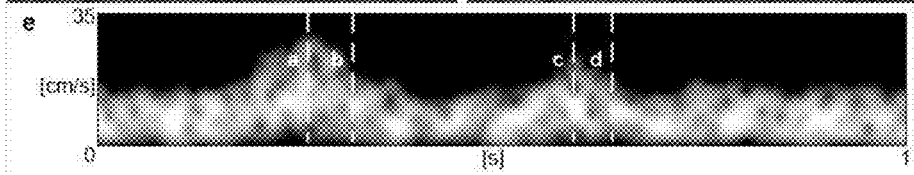
FIG. 7E shows the relative positions in the pulse cycle in a Doppler spectrogram.

Using the VPI technique, time-resolved quantitative visualization of multi-directional and spatiotemporally varying flow patterns that emerge within curvy vasculature under pulsatile flow conditions were achieved for a healthy carotid bifurcation with 72 bpm pulse rate. As an illustration, FIG. 6 shows the long-axis view of the flow dynamics inside a healthy carotid bifurcation phantom. In particular FIGS. 6A, 6B, 6C, AND 6D are still frame VPI renderings showing the formation and dissipation of a flow disturbance in a healthy carotid bifurcation phantom. Frames for four time points are shown, i.e., FIG. 6A is for peak systole; FIG. 6B shows the end of the post-systolic down stroke; FIG. 6C is the dicrotic wave peak; and FIG. 6D shows the end of dicrotic wave. The relative positions in the pulse cycle are marked in the Doppler spectrogram shown in FIG. 6E, which was obtained from a 1×1 mm sample volume placed at the CCA center. The nominal VPI frame rate ($f_{VPI}$) and the playback rate were 416 fps and 50 fps, respectively (generated from $f_{DAQ}$ of 3,333 Hz for a three-Tx, three-Rx VPI configuration). Multi-directional and spatiotemporal variations in the flow pattern are coherently depicted. Also rendered is the flow disturbance 60 in the ICA carotid bulb.

The nominal VPI frame rate ($f_{VPI}$) was 416 fps, and it was played back at 50 fps ($f_{DAQ}$ was 3,333 Hz). The rendered flow dynamics were found to be consistent with well-established findings obtained from computational predictions See, Berger S A, Jou L D, "Flows in stenotic vessels," *Annu. Rev. Fluid Mech.*, (2000) 32: 347-382). In particular, it can be readily observed that the temporal evolution of flow speed and flow direction rendered by VPI in different parts of the vasculature are, as expected, synchronized with the stroke of the flow pulse. Also, in the ECA branch (lower branch), streamlined forward flow (without reversal) along the vasculature was evident throughout the pulse cycle. This latter observation effectively demonstrates that VPI's flow vector estimation procedure is robust against flow angle variations, which do arise in the ECA as its inlet segment is inherently tortuous.

The technical merit of VPI is perhaps more notably demonstrated by its rendering of flow disturbances in the ICA branch of the healthy carotid bifurcation. This branch corresponds to the upper branch in FIG. 6. As visualized, while flow remained laminar on the inner wall side of the ICA sinus, the flow pattern on its outer wall side (where the carotid bulb is located) exhibited recirculation behaviour as highlighted by VPI's vortical projectile motion at 60. Such a flow disturbance phenomenon was found to be transitory in nature. In particular, it only emerged in certain phases of the pulse cycle.

The millisecond time resolution (2.4 ms for 416 fps nominal frame rate) of VPI effectively enabled tracking of when a flow disturbance emerged in the carotid bulb of the healthy bifurcation vasculature. FIG. 6 shows a series of key VPI frames that representatively depict this time-varying flow disturbance trend (the corresponding pulse cycle phase of each frame is marked on the pulsed Doppler spectrogram of the CCA shown in FIG. 6E. During peak systole (FIG. 6A), flow in the carotid bulb region was in the forward direction. However, in the post-systolic down stroke phase (FIG. 6B), a flow recirculation zone A appeared in this part of the ICA sinus. It subsequently dissipated during the dicrotic wave that produced a secondary flow upstroke (FIG. 6C), and flow was again moving forward in this phase of the pulse cycle. At the conclusion of the dicrotic wave, which was preceded by a secondary down stroke, vortical flow B emerged once more (FIG. 6D).

To further demonstrate VPI's efficacy in accurately visualizing highly complex flow dynamics, FIG. 7 shows still frames of a VPI cineloop of the long-axis view of a diseased carotid bifurcation phantom with 50% eccentric stenosis at the entrance to the ICA branch (obtained using same imaging parameters as before). In particular, FIG. 7 reveals spatiotemporal differences in the two post-stenotic flow recirculation zones in the carotid bifurcation phantom with 50% ICA eccentric stenosis. The trend is highlighted by VPI frames at four instants: FIG. 7A peak systole; FIG. 7B arrival of post-systolic jet front at ICA distal end; FIG. 7C dicrotic wave peak; and FIG. 7D arrival of post-dicrotic jet front at ICA distal end. Reference times are marked in FIG. 7E that shows the Doppler spectrogram for a range gate at the CCA center (1×1 mm sample volume size). VPI can effectively highlight high-speed flow jet and flow recirculation zones in a diseased carotid bifurcation phantom with 50% eccentric stenosis at ICA inlet (long-axis view). Imaging parameters are the same as for FIG. 6 ($f_{VPI}$: 416 fps; playback rate: 50 fps). Time-course dynamics of flow disturbance in the two recirculation zones are shown in greater detail in the two enlarged windows.

One striking observation to be noted is that, during systolic upstroke, the formation of a high-velocity flow jet (red arrows) can be dynamically visualized at the site of stenosis. Indeed, the flow jet continued to propagate along the inner wall side of the ICA sinus (i.e. the unstenosed side) and spurted across the ICA lumen. It then collided against the outer ICA wall near the distal end of the carotid bulb where the ICA vessel started to become straightened. Upon hitting the outer wall, the jet direction was reoriented tangentially against the wall and eventually ramped off before it dissipated further downstream.

In FIG. 7, another key feature visualized by VPI is the presence of two flow recirculation zones on the two flanks of the post-stenotic flow jet which traversed across the ICA lumen. One of the zones was located in the carotid bulb region C, while the other D was along the inner wall segment immediately below the curvature of the dissipating flow jet after it ramped off the outer wall. This observation is in close match with the findings derived from flow simulation studies (Steinman et al. 2000) and particle image velocimetry experiments (Kefayati and Poepping 2013; cited above and Poepping T L, Rankin R N, Holdsworth D W, "Flow patterns in carotid bifurcation models using pulsed Doppler ultrasound: effect of concentric vs. eccentric stenosis on turbulence and recirculation," *Ultrasound Med. Biol.*, (2010) 36: 1125-1134.).

As illustrated in FIG. 7, which shows the four representative VPI frames of the stenosed bifurcation phantom, the two recirculation zones were found to distinctly differ in spatiotemporal characteristics. For the one at the carotid bulb C, the vortical spin is sustained over the entire pulse cycle without dissolution. In contrast, the flow recirculation zone D at the inner wall segment had formed and shed twice within the same cycle, and it emerged when surrounded by a flow jet arch which created a substantial fluidic shear force due to the high velocity gradient at the zone boundary. Note that such an arch was not formed when the primary and secondary flow jets initially emerged at the site of stenosis respectively during peak systole (FIG. 7A) and at the dicrotic wave peak (FIG. 7C). It only appeared after the jet front had completed its propagation from the stenosis site to the distal end of the ICA, thereby encircling the slow-flow components adjacent to the inner wall (FIGS. 7B and 7D).

Using ultrasound to visualize complex flow dynamics is inherently not a straightforward task. In developing a prospective solution, two practical vascular flow conditions must be taken into account: (i) at a given time instant, flow speed and direction (i.e. the flow vector) may vary spatially because of the tortuous nature of vascular geometry; and (ii) over a cardiac pulse cycle, flow components would deviate temporally due to pulsatile behaviour. VPI has been designed to capture and render these spatiotemporal dynamics in blood flow.

From a technical standpoint, VPI is equipped with three key features that enable time-resolved visualization of flow vectors over an imaging view. First, it performs high-frame-rate broad-view data acquisition via multi-angle plane wave imaging principles, so as to achieve the high time resolution required to monitor flow pulsations and their spatial variations over an imaging view (FIG. 1). Second, VPI uses a customized multi-Tx, multi-Rx Doppler analysis framework to calculate flow vectors at different pixel positions and at each time instant (FIG. 2); robust estimation performance is attained by incorporating post-hoc regularization (flow region detection, phase unwrapping) and least-squares fitting principles during flow vector computation. Third, VPI dynamically renders flow vectors in the form of color-encoded particle projectiles whose trajectory is depicted through inter-frame updates of projectile position (FIG. 3). Dynamic flow perception is enhanced through adjunct display of grayscale flow speckles.

The practical merit of VPI in visualizing complex flow dynamics is demonstrated through a carotid bifurcation phantom study with controlled flow conditions that are otherwise not possible in-vivo (FIG. 4). In the case of healthy bifurcation geometry, not only is VPI capable of accurately tracking pulsatile streamlined flow (FIG. 6), it also depicts the transient presence of flow recirculation in the carotid bulb during the primary and secondary down stroke phases of the carotid pulse cycle (FIG. 6). The visualization performance of VPI is even more clearly made evident in the carotid bifurcation geometry with 50% eccentric stenosis. In particular, this new technique effectively highlighted the high-speed flow jet emerging from the stenosis site and its trajectory (FIG. 7). Also, it enabled time-resolved observation of the flow disturbance zones in the carotid bulb region and along the ICA inner wall segment (FIG. 7), both of which were known characteristics of stenosed ICA branches (Kefayati and Poepping 2013; Poepping et al. 2010). The present invention is the first in which such complex flow features are being imaged via ultrasound-based techniques.

Figure 8A:
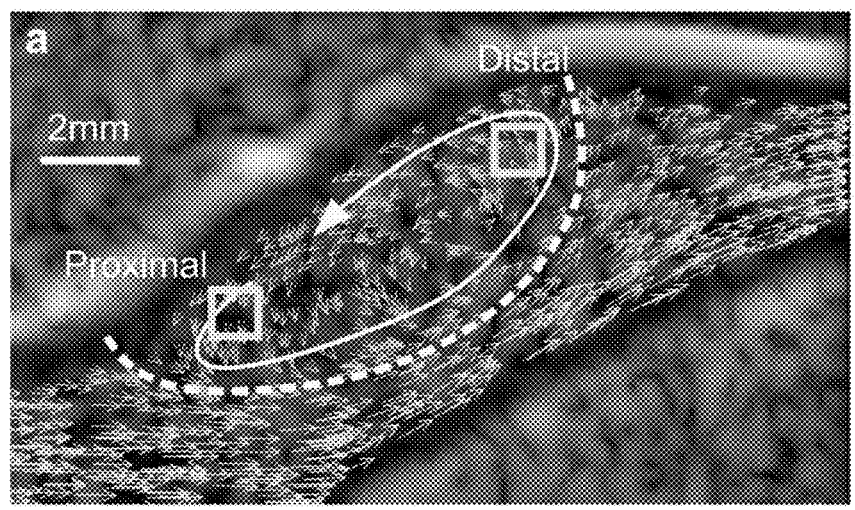
Figure 8B:
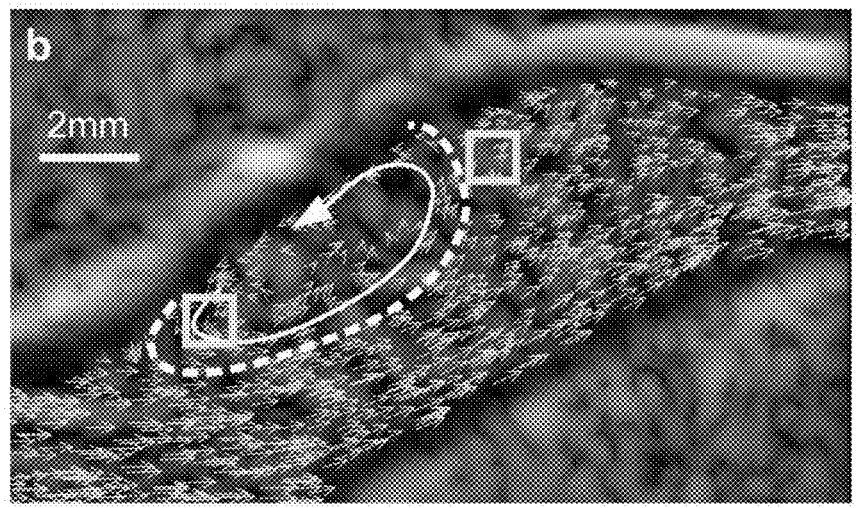
Figure 8C:
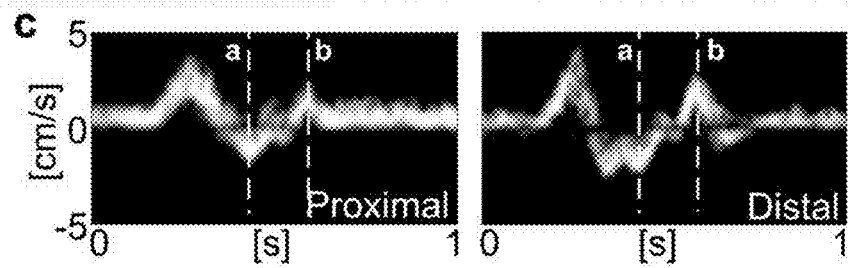
FIG. 8C shows the corresponding instants in two Doppler spectrograms when these two images occur in the pulse cycle.

As an integrative insight into VPI's application potential in delineating specific details of complex flow patterns, FIG. 8 summarizes the flow disturbance trends in the healthy carotid bifurcation phantom as observed by this imaging framework. FIGS. 8A and 8B show two enlarged views of the ICA which demonstrate VPI's ability to resolve complex flow details. Two frames are shown here to depict differences in the spatial-peak size of flow recirculation zones observed in FIG. 8A after systole and FIG. 8B after dicrotic wave in the carotid bulb of the healthy bifurcation phantom. The corresponding instants of these two frames in the pulse cycle are labeled in the two Doppler spectrograms shown in FIG. 8C, which are extracted from 1×1 mm sample volumes respectively in the proximal and distal ends of the carotid bulb [position marked by yellow boxes in FIGS. 8A, 8B].

In the case of healthy bifurcation, it should be noted that the recirculation zone in the carotid bulb region is larger at the end of post-systolic down stroke (FIG. 8A) in comparison to that at the end of dicrotic wave (FIG. 8B). In particular, as marked in these two frames (white dashed line; drawn based on manual inspection), the zone boundary was spanned over the entire carotid bulb region during the post-systolic down stroke phase likely because of the rapid flow deceleration, whereas at the end of the dicrotic wave, the recirculation zone only emerged in the region proximal to the ICA inlet given the gentler down stroke. This visualization matches well with the Doppler spectrograms (FIG. 8C) extracted from ranged gates at the proximal and distal ends of the carotid bulb, where quad-phasic and tri-phasic flow were observed respectively.

FIG. 9 shows VPI-guided analysis of spatiotemporal characteristics of flow recirculation zones in the 50%-stenosed bifurcation phantom. In particular, FIG. 9A and FIG. 9B respectively show recirculation patterns in the carotid bulb during peak systole and dicrotic wave peak. The relative time instant of these two frames is marked in the two Doppler spectrograms shown in FIG. 9C, which are taken from the flow jet and the distal end of carotid bulb [yellow boxes in FIGS. 9A and 9B]. For the recirculation zone adjacent to the ICA inner wall, its spatial-peak size is highlighted by two VPI frames taken during: systole FIG. 9D; dicrotic wave FIG. 9D. For reference, Doppler spectrograms are shown in FIG. 9F for two sample volumes placed at the proximal and distal ends of the ICA inner wall.

For the stenosed carotid bifurcation, the spatial extent of its two flow recirculation zones shows substantial differences. While VPI did not detect significant changes in the size of the carotid bulb recirculation zone over the pulse cycle (FIGS. 9A and 9B), this new imaging tool did reveal size variations for the flow recirculation zone at the ICA inner wall (FIGS. 9D and 9E). Specifically, the primary flow jet arch produced during systole was found to generate a larger flow recirculation zone along ICA inner wall, whereas the secondary arch arising from the dicrotic wave only created a smaller one likely because the fluidic shear force was smaller due to the slower jet speed. Such a finding can be confirmed by the Doppler spectrograms (FIG. 9F) obtained from range gates placed adjacent to the proximal and distal sections of the ICA inner wall where the temporal flow profiles were respectively quad-phasic and tri-phasic in nature. In contrast, for a range gate placed within the carotid bulb recirculation zone, its Doppler spectrogram was found to be monophasic and was reciprocal in appearance with respect to that for a range gate placed in the flow jet region (FIG. 9C).

As mentioned above, the adjunct display of grayscale flow speckles can enhance the flow visualization performance of the algorithm because inter-frame flow speckle displacements can serve to highlight the flow trajectory path. FIG. 4B illustrates a healthy carotid bifurcation scenario without any visualization enhancement. FIG. 12 shows a set of flow speckle frames (12A, 12B, 12C, and 12D) displayed without the vector projectiles. When visualized in the form of a high frame rate cineloop well beyond the video display range, these flow speckles would displace coherently in between frames according to the pulsatile flow pattern. This form of rendering would depict the flow trajectory accordingly. In turn, when displayed concurrently with the vector projectiles, they would provide a secondary visualization channel for complex flow information.

FIG. 13 shows the same flow as in FIG. 12, but in this case the vector projectiles are shown without the speckles (13A, 13B, 13C, and 13D). The finished display with speckles and projectiles is shown in FIG. 6.

Being a newly developed technique with fine temporal resolution and flow vector estimation capabilities, VPI can be leveraged to investigate various forms of complex flow dynamics. For instance, besides using VPI to study flow patterns in the carotid bifurcation as demonstrated here, this technique can be used to examine multi-directional flow dynamics inside diseased vascular features such as aneurysms. Also, VPI can be applied to visualize flow turbulence with fluttering features that require fine temporal resolution to render coherently. Realizing these applications would effectively substantiate the diagnostic value of VPI in complex flow analysis.

As the fine temporal resolution offered by VPI hinges on the use of broad-view data acquisition sequences in which the ultrasound firings are unfocused in nature, the flow signals returned from deeper vasculatures would inevitably be weaker as a consequence. This issue, which would be physically worsened by depth dependent attenuation, may pose a challenge when diagnosing certain patients whose vasculature tends to be positioned farther away from the skin surface. Hence, flow signal enhancement techniques may be used to reinforce the efficacy of the VPI framework when used in different in-vivo scan settings. One particular strategy that can be used is the incorporation of coded excitation principles into the transmission pulse sequence design. See Zhao H, Mo L Y L, Gao S, "Barker-coded ultrasound color flow imaging: Theoretical and practical design considerations," *IEEE Trans Ultrason Ferroelectr Freq Control* (2007), 54:319-331, which is incorporated herein in its entirety. Alternatively, microbubble contrast agents may be introduced to boost the flow signal level when performing VPI. See, Tremblay-Darveau C, Williams R, Milot L, Bruce M, Burns P N, "Ultrafast Doppler imaging of microbubbles," *In Proceedings* 2012 *IEEE Ultrasonics Symposium*, Dresden, Germany, 7-10 October. New York: IEEE; (2012), p. 1315-1318.

Another aspect of VPI to be further refined is its engineering considerations regarding the technique's real time realization. In the arrangement of FIG. 10, real-time GPU-based beam formers were leveraged, but the data were processed off-line because the scanner hardware was based on the use of a universal serial bus data transfer link whose bandwidth was inadequate for real-time streaming. To effectively facilitate on-line execution of VPI, a high-speed data transfer connection (e.g., Peripheral Component Interconnect Express links) may be used, e.g., with ultrasound scanner architectures that support channel-domain data streaming at real-time throughputs. See, Diagle R E, Kaczdowski P J, "High frame rate quantitative Doppler flow imaging using unfocused transmit beams," U.S. patent application Ser. No. 12/490,780 (2009); and Walczak M, Lewandowski M, Zolek N, "Optimization of real-time ultrasound PCI e data streaming and Open CL processing for SAFT imaging," *In Proceedings,* 2013 *IEEE Ultrasonics Symposium*, Prague, Czech Republic, 21-25 July. New York: IEEE; (2013), both of which are incorporated herein in their entirety.

Alternatively, VPI can be further used for echocardiography investigations where vector visualization of intracardiac flow fields currently relies on either post-processing of color flow imaging data or the use of microbubble contrast agents to perform echo particle image velocimetry. To realize VPI for echocardiography applications, the flow vector estimation framework would need to be further refined to account for the non-stationary tissue clutter that arises due to myocardial contraction. For instance, when deriving the frequency shift estimates of each Tx-Rx angle pair, advanced signal processing solutions that are resilient against tissue motion biases could be adapted for this purpose, such as maximum likelihood estimation and adaptive-rank eigen-estimation. See, Lovstakken L, Bjaerum S, Torp H, "Optimal velocity estimation in ultrasound color flow imaging in presence of clutter," *IEEE Trans. Ultrason. Ferroelec. Freq. Contr.*, (2007), 54: 539-549; and Yu A C H, Cobbold R S C, "Single-ensemble-based eigen-processing methods for color flow imaging—Part II. The matrix pencil estimator," *IEEE Trans. Ultrason. Ferroelec. Freq. Contr.*, (2008), 55: 573-587, both of which are incorporated herein in their entirety.

VPI can be considered a new approach in leveraging ultrasound for flow estimation purposes. In particular, it represents a drastic transformation in the way that flow information is acquired, estimated, and rendered in comparison to conventional color flow imaging. Since VPI is essentially non-invasive, this technique should hold promise in being introduced as a routine diagnostic tool to investigate complex flow dynamics in the human vasculature. For instance, in the context of carotid diagnostics, VPI can potentially be adopted as a more instinctive way to assess the severity of carotid stenosis compared with the conventional Doppler spectrogram mode that is routinely performed as part of the clinical practice for carotid disease management. If such clinical translation effort can be realized, the present role of ultrasound in vascular diagnostics can undoubtedly be expanded.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

The invention claimed is:

1. An ultrasound imaging system comprising:
a data acquisition unit, which transmits, via an ultrasonic array transducer, a series of plane waves into a tissue and receives waves reflected from the tissue to obtain beam-formed data frames;
a flow vector estimation unit which estimates flow vectors at pixels of the data frames using data of the data frames; and
a display rendering circuit which displays, on a display, the flow vectors estimated as color coded moving projectiles having varying lengths and colors themselves across the moving projectiles based on velocity magnitudes of one or more flow vectors of the flow vectors corresponding to the moving projectiles, wherein positions of the projectiles are dynamically updated between data frames based on axial lateral velocities of the projectiles representing the corresponding flow vectors across the data frames and one or more inter-frame periods between the data frames to depict movement of the projectiles corresponding to one or more flow patterns in the tissue.

2. The system of claim 1, wherein projectile length of the projectiles are set based on velocity magnitudes at the pixels.

3. The system of claim 1, wherein direction of the projectiles shows flow direction at the pixels.

4. The system of claim 1, wherein the display rendering circuit displaying the flow vectors estimated as moving projectiles comprises:
selecting a set of pixels in a data frame as projectile launch points;
displaying the flow vectors at the set of pixels selected as projectiles;
calculating incremental displacement of the next frame based on the corresponding axial-lateral velocities of the projectiles and the one or more inter-frame periods;
updating positions of projectiles in the next frame based on the displacement calculated; and
displaying projectiles of the next frame at the positions updated.

5. The system of claim 1, wherein a projectile is displayed only if a corresponding pixel position used to estimate one or more flow vectors for the projectile falls within a flow region.

6. The system of claim 1, wherein, when a corresponding pixel position used to estimate one or more flow vectors of a projectile does not fall within a flow region, a new projectile is regenerated at an original projectile launch point where the projectile was first created.

7. The system of claim 1, wherein the display rendering circuit further displays grayscale flow speckles together with the projectiles.

8. An ultrasound imaging method, comprising:
transmitting, via an ultrasonic array transducer, a series of plane waves into a tissue and receiving waves reflected from the tissue to obtain beam-formed data frames;
estimating flow vectors at pixels of the data frames using data of the data frames; and
displaying, on a display, the flow vectors estimated as color coded moving projectiles having varying lengths and colors themselves across the moving projectiles based on velocity magnitudes of one or more flow vectors of the flow vectors corresponding to the moving projectiles, wherein positions of the projectiles are dynamically updated between data frames based on axial lateral velocities of the projectiles representing the corresponding flow vectors across the data frames and one or more inter-frame periods between the data frames to depict movement of the projectiles corresponding to one or more flow patterns in the tissue.

9. The method of claim 8, wherein projectile length of the projectiles are set based on velocity magnitudes at the pixels.

10. The method of claim 8, wherein direction of the projectiles shows flow direction at the pixels.

11. The method of claim 8, wherein displaying the flow vectors estimated as moving projectiles comprises:
selecting a set of pixels in a data frame as projectile launch points;
displaying the flow vectors at the set of pixels selected as projectiles;
calculating incremental displacement of the next frame based on the corresponding axial-lateral velocities of the projectiles and the one or more inter-frame periods;
updating positions of projectiles in the next frame based on the displacement calculated; and
displaying projectiles of the next frame at the positions updated.

12. The method of claim 8, wherein a projectile is displayed only if a corresponding pixel position used to estimate one or more flow vectors of the projectile falls within a flow region.

13. The method of claim 8, wherein, when a corresponding pixel position used to estimate one or more flow vectors of a projectile does not fall within a flow region, a new projectile is regenerated at an original projectile launch point where the projectile was first created.

14. The method of claim 8, further comprising displaying grayscale flow speckles together with the projectiles.

* * * * *